(12) United States Patent
Miller

(10) Patent No.: US 10,130,317 B2
(45) Date of Patent: Nov. 20, 2018

(54) INTRAORAL DENTAL RADIOLOGICAL IMAGING SENSOR

(71) Applicant: Todd Miller, San Jose, CA (US)

(72) Inventor: Todd Miller, San Jose, CA (US)

(*) Notice: Subject to any disclaimer, the term of this patent is extended or adjusted under 35 U.S.C. 154(b) by 0 days.

(21) Appl. No.: 15/180,680

(22) Filed: Jun. 13, 2016

(65) Prior Publication Data

US 2018/0064405 A1    Mar. 8, 2018

(51) Int. Cl.
*A61B 6/14* (2006.01)
*H01L 27/146* (2006.01)
*H01L 27/148* (2006.01)
*H01L 23/00* (2006.01)

(52) U.S. Cl.
CPC ............. *A61B 6/145* (2013.01); *H01L 24/48* (2013.01); *H01L 27/14636* (2013.01); *H01L 27/14661* (2013.01); *H01L 27/14663* (2013.01); *H01L 27/14831* (2013.01); *H01L 2224/48227* (2013.01)

(58) Field of Classification Search
None
See application file for complete search history.

(56) References Cited

U.S. PATENT DOCUMENTS 6,042,267 A * 3/2000 Muraki ................. G01T 1/2018
                                                    348/E5.086
7,151,263 B2 * 12/2006 Homme .................... G01T 1/20
                                                    250/370.11

2017/0164914 A1 * 6/2017 Kravis ................... A61B 6/145

* cited by examiner

*Primary Examiner* — Hoon Song
(74) *Attorney, Agent, or Firm* — W. Edward Johansen

(57) ABSTRACT

An intraoral x-ray imaging sensor includes an electronic interface substrate which has a first surface and a second surface and is substantially rectangular with a mesial end and a distal end and a semiconductor imager which is mechanically and electrically coupled to the electronic interface substrate and which has a first surface and a second surface. The semiconductor imager consists of a silicon layer having an array of detector elements formed on its the first surface and is substantially rectangular with a mesial end and a distal end. The electronic interface substrate and the semiconductor imager have a first cut corner and a second cut corner at its the distal end. The second surface of the semiconductor imager is disposed adjacent and contiguous to the first surface of the electronic interface substrate. The intraoral x-ray imaging sensor also includes a plurality of first electrical pads, a plurality of second electrical pads and a plurality of bond wires. The first electrical pads are disposed on the first surface of the electronic interface substrate wherein some of the first electrical pads are disposed adjacent and contiguous to the first cut corner and the remainder of the first electrical pads are disposed adjacent and contiguous to the second cut corner. The second electrical pads are disposed on the first surface of the semiconductor imager wherein some of the of second electrical pads are disposed adjacent and contiguous to the first cut corner and the remainder of the second electrical pads are disposed adjacent and contiguous to the second cut corner. Each bond wire electrically couples one of the first electrical pads to one of the second electrical pads.

18 Claims, 22 Drawing Sheets

INTRAORAL DENTAL RADIOLOGICAL IMAGING SENSOR

BACKGROUND OF THE INVENTION

Field of the Invention

The present invention relates to intraoral radiographic imaging sensors and more particularly to an intraoral radiographic imaging sensor which not only decreases dead space, but also increases a patient's comfort.

Description of the Prior Art

X-rays have been used in dentistry to image teeth and parts of the mouth for many years. In general, the process involves generating x-rays and directing the x-rays at the patient's mouth. The x-rays are attenuated differently by different parts of the mouth (e.g., bone versus tissue) and this difference in attenuation is used to create an image, such as on film or by using electronic image sensor. Radiographs are fundamental to most dental diagnostic procedures. A common complaint and problem during radiographic exams is patient discomfort during the placement of radiographic sensors within the mouth. The majority of these complaints involve the placement of the radiographic sensor in the posterior maxillary and mandibular arches of the patient. This problem is primarily due to the limited space available for proper placement of the sensors within these regions. This has been a problem since the inception of dental radiography using standard x-ray film technology.

Recently, solid-state x-ray sensors have been developed that replace film. The patient discomfort problem for these sensors is even greater because these devices are rigid by nature and cannot be bent like film to conform to the patient's anatomy.

Referring to FIG. 1 a dental x-ray system 10 which U.S. Pat. No. 9,259,197 teaches and which includes an x-ray source 12 which is located on an end 13 of a mechanical arm 15. When activated, the x-ray source 12 generates an x-ray stream 16 that has a generally circular cross-section. In many applications, a collimator 17 is used to reduce the size of the stream and generate a smaller x-ray stream having a rectangular cross-section. The collimator 17 may be used with a mechanical positioning device to help align the x-ray stream with an x-ray sensor. The x-ray source 12 is positioned by an operator so that the x-ray stream 16 is directed to an intraoral sensor 20. The intraoral sensor 20 is shown located in the mouth of a patient 21. The intraoral sensor 20 may include a scintillator that coverts x-ray radiation to visible light. The sensor 20 may be configured to convert x-rays into electric charge without a scintillator. The sensor 20 also includes an array of pixels 22. The components of FIG. 1a, including the array of pixels 22, are not drawn to scale relative to the outline of the sensor 20. Each pixel produces an electric signal in response to light (from the scintillator) or x-ray radiation impinged upon it. The sensor 20 may include one or more "on-board" analog-to-digital converters to covert analog signals generated by the pixels to digital signals. These signals are provided to a processor 23 such as a programmable, electronic microprocessor, field programmable gate array, erasable programmable logic device(s), or similar device(s). The processor 23 is connected to memory 24 (ROM and RAM) and an input-output interface 25. The sensor 20 also includes one or more electronic circuits for power supply, driving the array of pixels, and driving the output (e.g., circuits located in the I/O interface 25). The I/O interface 25 may be a universal serial bus ("USB") interface. The processor 23 controls image capture or triggering of the sensor 20. The x-ray source 12 is coupled to the sensor 20, e.g., via computer 30, such that when the x-ray source 12 is activated, a command is sent simultaneously or nearly simultaneously to the sensor 20 to perform an image capture. It is possible to generate a burst of x-ray radiation and be assured that an image will be captured by the sensor 20 during the relatively short period of x-ray exposure either through automatic triggering or via a specific capture command sent to the intraoral sensor 20.

Referring back to FIG. 1 a wire, cable, or similar connector 27 of the sensor 20 connects the sensor 20 to a computer 30. The computer 30 includes a processor 32, an input/output interface 34, and memory 36 (e.g., RAM and ROM). The input/output interface 34 may be a USB connection and the cable 27 may be a USB cable. Image data captured by the sensor 20 and processed by the computer 30 is sent to a display 38 and viewed as image 40. The location of the intraoral sensor 20 in the patient's mouth determines what part of the patient's anatomy can be imaged, e.g., the upper jaw versus the lower jaw or the incisors versus the molars. An x-ray operator places (or assists the patient in placing) the intraoral sensor 20 at a desired location with the patient's mouth. Various sensor holders including those that are used with or that include a collimator may be used to keep the sensor 20 in the desired location until an image is created or captured. Some holders are designed so that the patient bites the holder with his or her teeth and maintain the position of the sensor 20 by maintaining a bite on the holder. After the sensor 20 is positioned behind the desired anatomical structure, and the x-ray field to be generated by the x-ray source 12 is aligned with the sensor 20, it is possible that the source 12 and sensor 20 will, nevertheless, become misaligned. Misalignment can be caused by the patient moving his or her head, moving the intraoral sensor 20 by re-biting the holder, moving his or her tongue, etc. and other causes.

Referring to FIG. 3 in conjunction with FIG. 1 and FIG. 2 the sensor 20 includes a housing 45 which has a top portion 50 and a bottom portion 55. Within the housing 45 is an insulator 60, a printed circuit board (printed circuit board) 65, a silicon detecting layer 67 and an x-ray converter 70. The sensor 20 may include a cushioning layer 71 which protects against mechanical shocks. The top portion 50 includes a dome 75 that receives the cable 27. The dome 75 includes a face with an approximately circular opening through which the cable 27 passes. The cable 27 includes connectors (e.g., wires), a portion of which pass through an opening 79 of the insulator 60 to connect to the printed circuit board 65. A ribbon or other connector may pass through the opening 79 to couple the wires of cable 27 to the printed circuit board 65. The insulator 60 provide electrical isolation between the printed circuit board 65 and the housing 45 of the sensor 20. The insulator 60 may also secure the printed circuit board 65 and x-ray converter 70 in position and protect each against mechanical shocks. Although the insulator 60 resists conducting electricity it is a conductor of heat and assists in transferring heat away from the printed circuit board 65. Not only does the sensor 20 include the printed circuit board 65, silicon detecting layer 67 and the converter 70, but it also includes the array of pixels 22, the processor 23, the memory 24 and I/O interface 25. The array of pixels 22 includes a plurality of pixels. Each pixel may include a converting portion (i.e., a portion of converter 70) and a detecting portion (i.e., a portion of silicon detecting layer 67). The printed circuit board 65 supports the silicon detecting layer 67 (e.g., either a CMOS die or a CCD device) and the converter 70 with the silicon detecting layer 67 being secured using a glue or epoxy to the printed circuit board 65. The converter 70 converts x-rays received through the bottom portion 55 into light. The light travels to the silicon detecting layer 67, which converts the received light into charge. The charge is integrated at each pixel and the quantity of charge integrated represents the amount of x-rays received (although some of the integrated charge is attributable to noise and dark current). During a read-out of the array of pixels 22, the processor 23 determines the quantity of charge integrated at each pixel in the array of pixels 22. The converter 70 and silicon detecting layer 67 may include a fiber optic with scintillator. The array of pixels 22 may convert x-rays directly to charge without an intermediate step of converting x-ray to light.

U.S. Pat. No. 5,510,623 teaches a solid state image sensor CCD array which has a two block, full-frame, parallel-register structure. The two blocks of the array, each comprised of photosensitive radiation sensors or pixels, feed into a single centrally disposed serial read-out register so as to form one unified photosensitive domain. The read-out register is photosensitive except for two associated narrow clock buses that are spaced apart so as to only block a minimum of input radiation in any one pixel of the read-out register. Each stage of the read-out register can act as a pixel that is approximately square and that is approximately the same size as the pixels of the two full-frame blocks. In operation, the centrally disposed read-out register can be stationary for a significant first portion of a total frame time (integration period), and then in a latter part of the frame time it can be read out one or more times to provide exposure update information for all of the pixels of the array. Typical examples of applications include advanced histogram-based, or other types of, x-ray exposure optimization. The array avoids the use of an "amplifier corner" that is characteristic of most if not all area image sensors. As such, all four corners of the array can be shaped to suit a particular application. One application of particular interest is for intraoral dental x-ray imager and system.

Referring to FIG. 4 an x-ray silicon image sensor chip which U.S. Pat. No. 5,510,623 teaches. The x-ray silicon image sensor chip is used as an intraoral x-ray image sensor. The silicon image sensor chip is a silicon-based CCD having an area array a consisting of individual pixels that are approximately 40 microns by 40 microns square. The CCD gate structure is generally fabricated using three successive polysilicon (poly) depositions. The overall active sensing area is a rectangular region approximately 25 millimeters by 30 millimeters. All four corners of the array a are chamfered (or beveled). The approximate array size is 640 pixels by 800 pixels. A substrate or carrier 112 on which the Si CCD area array a is mounted. The corners of the carrier 112 are also beveled to match the corners of the array a. The diagonal dimensions of the array a and the carrier 12 are thus both beneficially reduced by approximately % due to the beveling of the array a and the carrier 112. The array a includes a centrally disposed photosensitive read-out register b (also referred to herein as a horizontal (H) register) that is coupled to an output charge-sensing preamplifier (preamp) c. The preamp c converts a magnitude of a charge packet to a corresponding voltage potential. The read-out register b is placed so as to divide or partition the active area of the array a into two halves (referred to herein for convenience as left and right halves or as top and bottom halves). A plurality of terminals d are disposed along one edge of the array a, and are wire-bonded to corresponding terminals 112a on the carrier 112. Wiring 114 is connected to the terminals 112a for connecting the array a to suitable DC operating power, biases, clock signals, and for outputting the charge signals from preamp c. The charge signals are read-out of the array a either after an exposure or during the exposure. The CCD read-out structure is disposed at an interior region of the array, in this case in the center (read-out register b), as opposed to along edges that extend to rectangular corners of the array. Only the preamp c is located at an edge of the array, with the preamp being disposed at one end of the readout register b, away from the corners, as opposed to being located in a corner. This enables the outer edges of the array a to be shaped as desired. For example, a regular octagon shape can be used wherein each edge is equal in length to all other edges.

U.S. Pat. No. 7,916,200 teaches an image sensor with corner cuts which includes a matrix of horizontal lines and vertical columns of photosensitive members, the matrix having a generally rectangular shape of horizontal width and having four bevels. The sensor includes as many current or voltage read blocks as there are matrix columns in order to read the image signals detected by the photosensitive members, characterized in that the current or voltage read blocks are placed in a row along a horizontal edge of the matrix of width and are all housed within a vertical strip. The width of which is substantially less than the maximum width of the matrix. There are two superposed rows of current read blocks with blocks distributed at the same pitch as the pixel columns, or there is a single row with read blocks distributed with a pitch less than that of the pixel columns. These image sensors are intended to be accommodated in areas where available space is reduced and for which the aim, nevertheless, is to have an image capture area that is as large as possible. This is the case for dental radiological image sensors because they must be accommodated in the mouth of a patient and the size of the image taken must correspond at least to the height of a tooth and the width of several teeth. The space constraints are therefore considerable and it is necessary to try to save as much as possible with regard to the volume of the sensor with a given image surface. The need for patient comfort entails additional ergonomic constraints. It has already been proposed to cut the corners of the package or make them round in order to improve the ergonomics and comfort in radiological image sensors which are made using CCD ("Charge Coupled Devices") technology. It has been proposed in this case to use a chip which itself has cut corners in order to prevent losing image capture surface. These sensors with chips having two cut corners with the two corners being located at the front in the direction in which the sensor is inserted into the mouth have been proposed. Sensors with four cut corners have also been proposed. This results in structure adjustments such as the installation of a charge reading register in the middle of the chip rather than on the edges. These adjustments are possible in CCD technologies. They are not possible in CMOS technologies, i.e. technologies in which the photosensitive members have active members made from MOS transistors at each pixel in order to convert the photo generated charges into voltage or current and in which the current or voltage signals corresponding to each pixel are transmitted on a column conductor linked with each column of pixels.

U.S. Patent Publication No. 2014/0023177 teaches a radiological image sensor which includes a housing, an electronic interface substrate, a semiconductor imager or imaging chip and a cable attached to the housing at a cable button connector. The semiconductor imager or imaging chip has electronics that create a dead space, with. The dead space is at a short distal side of the generally rectangular sensor opposite the short mesial side at which the cable exits the cable button connector. The mesial side of the sensor either does not have a dead space created by electronics of the imaging chip or the dead space found on the mesial side of the sensor is less than approximately 4 millimeters, and may be approximately 2 millimeters or less.

Referring to FIG. 5 in conjunction with FIG. 6 and FIG. 7 a radiological image sensor 201 which U.S. Patent Publication No. 2014/0023177 discloses as prior art. The radiological image sensor 201 has a cable side housing 210 connected to a front side housing 215 with a cable 206 running out of a cable button connector 211 in a front side housing 215 toward mesial side (MS) of the radiological image sensor 201. Inside the housing 210 moving from the cable side (CS) down to the front side (FS) are an electronic interface substrate 202 which includes electronic components 221 mounted on the cable side of a ceramic material 222, an imaging chip 203 which may be either a charge coupled device (CCD) or a CMOS imaging chip, a fiber optic face plate 204 which functions as an x-ray filter for improved noise reduction and a CSI scintillator 205 which is optimized for resolution and low noise. The radiological image sensor 201 has a generally rectangular shape. The shorter sides of the rectangle will always be defined by the direction in which the cable 206 exits the cable button connector 211. The mesial side will always be the side toward which the cable 206 exits the cable button connector 211 while the distal side will always be the side opposite which the cable 206 exits the cable button connector 211, even if the cable button connector 211 is not centered in the cable side housing 210. The electronic interface substrate 202 may have a shock absorption material around the periphery of the ceramic material 222.

Referring to FIG. 8 the space occupied by shock absorption material, as well as space occupied the sensor housing (once the cable side housing 210 and the front side housing 215 are assembled together), creates a dead space 208 in which a radiographic image is not obtained. The size of this dead space will typically be no less than 2 millimeters. In addition to the dead space 208, a second dead space 209 is created by the electronic components 231 located on the mesial side of imaging chip 203 in the radiological image sensor 201 which can represent another 4 millimeters or more of additional dead space. The combined effect of the dead spaces 208 and 209 in the intraoral radiographic sensors is an inability to duplicate the same coverage area in a patient's oral anatomy as x-ray film when placed in the exact same position relative to the patient's teeth. This problem is due to the intrinsic design and layout of all digital intraoral sensors with regard to the placement of the dead space that is created as a by-product by parts of the electronic on the sensor. Significantly, this 4-8 millimeter dead space is approximately the width of half to a whole canine, or premolar tooth.

Referring to FIG. 9 if the dead space 209 is moved to the distal side DS of the imaging chip 203 so that any dead space located on the mesial side of the sensor is kept to a bare minimum attributable solely to shock absorption material and the housing. Such a sensor design illustrates a cable side view of an electronic interface substrate 202 with dead space 209 being located at distal side DS, not mesial side. For purposes of orientation the cable 206 and cable button connector 211 are shown as trace lines.

Referring to FIG. 10 in conjunction with FIG. 9 a schematic diagram illustrates coverage Area A for a standard premolar bitewing film radiograph. Within Area A at its mesial side is another schematic diagram which illustrates coverage Area B and shows a typical loss of imaging area due to dead space for the sensor electronics for a digital sensor. If a digital dental sensor is placed in the exact position as the x-ray film, the resultant image will not show the first 4-8 mm of the mesial end of the patient's anatomy. Locating dead space 209 at distal side, contrary to current practices and traditional wisdom allows a dental practitioner to capture images not currently obtainable because Area B which represents a loss of imaging area due to dead space, is minimized, thus allowing greater capture of teeth located in the mesial area of a radiograph capture, which is especially important when a bitewing or periapical radiograph is being taken of the canine and premolar teeth. In this regard, some of the most painful radiographs captured are the premolar bitewing and posterior periapical views. The reason these radiographs are painful to take is that the imaging plate, whether a film or a sensor (which is stiffer and can cause more pain), must be located such that its mesial end is placed as far forward in the patient's mouth as possible to capture the distal aspect of the canine teeth and the mesial aspect of the premolar teeth in a bitewing or periapical view radiograph. Once the patient bites down the edges of the film or sensor dig into the tissue on the anterior ascending aspect of the maxillary palate or the lingual aspect of the anterior mandibular region; thus often causing pain when the mesial aspect of the digital sensor is impinging against these very sensitive anatomic regions during a radiographic exam. When a radiograph is being taken with a sensor with a cord, the sensor must be inserted to that the distal end is located towards the distal aspect of the teeth being imaged and then the mesial end is located at most mesial aspect of the teeth being imaged. By minimizing dead space at the mesial end MS of a sensor, the procedure for obtaining a radiograph of the patient's posterior teeth is far more comfortable and less painful, and better results are obtained.

Referring to FIG. 11 in conjunction with FIG. 12 and FIG. 13 a radiological imaging sensor includes an electronics substrate and an imaging chip held within an external housing or shell. The imaging chip has a specific shape and size. The shape of the electronic interface substrate will dictate the general shape and dimensions of the external housing or shell and its internal dimensions. Inside the sensor shell there is also internal free space for the mounting of shock absorbing structures and for the compression of the shock absorbing structures and resultant movement of the electronic substrate when the sensor is subjected to shock. The scintillator layer on the electronic interface substrate is very sensitive to shock which can result in irreversible damage and result a concomitant defect in the radiographic image. To increase the free space that surrounds the delicate electronics designers uniformly increase the entire internal and external dimensions of sensor housing in order to maintain uniform rectilinear dimensions of the overall sensor package. Such an approach is easy to design and easy to fabricate. However, shock damage to the scintillator layer is usually limited to the four corners of the electronic substrate and specifically to the two corners located at the sensor's distal end. This is mainly due to the fact that the sensor has an attached cable, therefore, when the sensor is accidentally dropped, the end which will impact first is usually biased toward the distal (non-cable end) of the sensor and usually impacts on the corner. This type of scintillator damage can be reduced by increasing the internal free space between the electronic interface substrate and the internal sides of the sensor shell which will result in an increase of the overall size of the sensor shell. Because this type of damage tends to be biased to the two distal corners, a sensor shell design that increases the free space only in a local region adjacent to the corners of the electronic substrate can decrease the probability of shock damage without increasing the overall size of the sensor shell. This local increase of the free space at two or more corners of the sensor shell can be achieved by either increasing both the external and internal dimension resulting in a local bulge of the sensor housing or only in the internal dimension of the sensor shell resulting in no external bulge in the sensor housing but rather an internal expanded pocket). This concept of local bulging or internal pocketing of the sensor housing can be applied to other sensitive structures on the electronic substrate such as on the flat back surface holding delicate electronics.

U.S. Patent Publication No. 2014/0367578 teaches an x-ray image sensor which includes an x-ray converter layer for converting x-rays into signals received by a semiconductor imager or detector for sampling and detecting converted x-rays as electrical signals, and an electronic interface or connection substrate including electrical connections, the x-ray converter layer bonded to a first surface of the semiconductor imager or detector and the electronic interface or connection substrate arranged at a second surface of the semiconductor imager detector opposite the x-ray converter layer. The semiconductor imager or detector in at least one edge portion includes vias for through-contacting detector elements formed in or on the first surface of the semiconductor imager or detector to the electronic interface or connection substrate. The x-ray converter layer may be any layer which converts x-ray radiation into signals which can be received and detected by a semiconductor material, in particular into optical radiation, i.e. radiation in the visible, UV or near IR portion of the electromagnetic spectrum, irrespective of the detailed structure and composition thereof. The x-ray converter layer consists of a fiber optic plate and a scintillating layer provided thereon. The semiconductor imager or detector is any element for detecting the signals provided by the x-ray converter layer, in particular the optical radiation generated in a scintillating layer into electrical signals on a pixel-basis, including an array of photoelectric detector or sensor elements, respectively. The semiconductor imager or detector converts the received signals into electrical signals. Well-known and commercially available semiconductor detectors are of the integrated silicon detector type (e.g. CCD or CMOS). The electronic interface or connection substrate includes connections and/or electronic components which are required for operating the semiconductor imager or detector component of the sensor and provides an internal signal processing as far as required irrespective of the specific type and manufacturing technology of the substrate. The electronic interface or connection substrate may include all types of printed circuit boards.

Referring to FIG. 14 in conjunction with FIG. 15 and FIG. 16 a prior art sensor includes a semiconductor imager or detector (silicon die) 310 of basically rectangular shape, with two corners chamfered, a conventional printed circuit board 320, and a fiber optic plate 330 with a scintillator layer 340 on that surface which is opposite to the surface where the silicon-die 310 together with the printed circuit board 320 are bonded to the fiber optic plate 330. The fiber optic plate 330 is acting as an x-ray blocking layer to absorb the x-ray intensity after the scintillating layer to prevent direct interaction of x-rays in the silicon-die 310 which would cause an undesired signal thereby degrading the performance of the sensor. Some of the prior art sensors have been built without using a fiber optic plate 330 by directly placing the scintillating layer onto the silicon-die 310. Older prior art sensors used the silicon die itself as a converting layer thereby accepting the weak performance efficiency of x-ray in silicon as compared to the better efficiency of newer prior art sensors, i.e. indirect working sensors using the combination of scintillating layer 340, x-ray blocking fiber optic plate 330 and silicon-die 310 optimized for the conversion of the optical signal generated in the scintillator by the x-ray signal. Typical prior art scintillator layers are made of thallium doped cesium iodide, which has a crystal structure and a thickness of around 100 microns. Scintillators and the interface to the fiber optic plate 330 (or silicon detector) are mechanically fragile. The fiber optics used in such sensors are much more mechanical stable due to their construction and their typical thickness of one to three mm. Hence, such fiber optics are inherently much less susceptible to damage induced mechanical stress. Wire bond connections 300 are provided to connect portions or functional elements on the light-receiving surface of the silicon-die 310 to connecting points on the printed circuit board 320, which is arranged on the opposite (back or bottom) surface of the silicon-die. It can be recognized that the wire bonds 300 are provided at one of the short edges of the silicon-die 310 and extend over that edge to a portion of the printed circuit board which projects over the edge of the silicon die. The fiber optic plate 330 with the scintillator layer 340 are basically congruent with the shape of the silicon-die 310, they are slightly recessed with respect to the silicon die, such that the fiber optic plate does not interfere with the wire bonds 300, which are raised above the upper surface of the silicon-die 310. Existing semiconductor detectors are such designed that all electrical connectivity, except the ground connection, must be implemented at one side of the detector thereby substantially limiting the freedom of designing the device. One challenge associated with electronic intraoral x-ray sensor is the limited space for obtaining optimized sensor signals. To provide images of high resolution and contrast. Insofar for such sensors it is required to optimize the ratio between that area of the sensor which is sensitive/receptive to x-ray radiation and an inactive area which is needed for electrically contacting, isolating and mechanically protecting the sensor. It is also a further challenge to provide for a high mechanical stability of the sensor under the constraints of limited space for the housing thereof and, more specifically of limited thickness of the sensor as a whole. The image sensor has the overall shape of a plate, and the semiconductor detector comprises a detector plate, the X-ray converter layer includes a fiber optic scintillating plate, and the connection substrate comprises a printed circuit board. The plate shape of the sensor components, as well as the corresponding overall shape of the sensor in its housing is, as such, a well-known configuration but is dramatically improved in its mechanical performance by applying the inventive concept. Techniques for forming via and through-contacts in a semiconductor substrate are well-known in the art, so that a detailed description of such techniques is not required. The semiconductor imager or detector includes a silicon wafer portion of basically rectangular shape, in particular with at least two corners cut-off (chamfered), four corners cut-off. the short edge of the rectangular side of the wafer portion, as well as two or all three edges of the chamfered-corner side are provided with via and through-contacts. The through-contacted detector elements are connected to the printed circuit board/substrate by wire bonds. Besides wire bonding, other well-established integrated circuit connecting techniques can be used to provide the required electrical connections between the detector elements and the associated connection points on the printed circuit board/substrate, including but not limited to ball bonding, soldering and galvanic techniques. The semiconductor imager or detector and the printed circuit board or electronic interface substrate are geometrically similar. The semiconductor imager or detector is slightly larger than the printed circuit board/substrate or are basically congruent. "Basically congruent" means that the circumferential shape of the semiconductor imager or detector and the printed circuit board or electronic interface substrate appear as identical although minor local deviations may exist. it is important that the printed circuit board or electronic interface substrate is not larger than the semiconductor imager or detector, i.e. the edges of the printed circuit board or electronic interface substrate do not project over the corresponding edges of the semiconductor imager detector thereby eliminating a drawback of prior art sensor arrangements. The x-ray converter layer, e.g. scintillating plate, and the semiconductor imager or detector are geometrically similar. The scintillating plate is slightly larger than the semiconductor imager detector and is arranged such that none of the edges of the semiconductor imager or detector projects over a corresponding edge of the scintillating plate. The scintillating plate protects the semiconductor imager or detector from external mechanical forces thereby helping to avoid damage of the fragile and expensive semiconductor imager or detector which is specifically a silicon wafer plate. The x-ray converter layer, e.g. the scintillating plate, is self-supporting. The x-ray converter layer, e.g. the scintillating plate, supports and provides mechanical integrity to the semiconductor imager detector and the printed circuit board or electronic interface substrate to which the x-ray converter layer, e.g. the scintillating plate, is tightly bonded. The tight bonding of the semiconductor imager or detector to the scintillating plate, notwithstanding the above mentioned slightly larger dimensions of the scintillating plate, becomes possible, or is at least facilitated, by the vias and through-contacts in the edge portions of the semiconductor imager or detector. The x-ray converter layer, e.g. scintillating plate, the semiconductor imager or detector and the printed circuit board or electronic interface substrate are as an integral mechanical unit encapsulated in a housing. The inner walls of the housing tightly fitting to the outer edges of the scintillating plate. The total area of the sensor including its housing, is minimized without increasing the risk of mechanical damage of the semiconductor imager or detector and/or the printed circuit board or electronic interface substrate. The optimized adapted housing guides mechanical impacts or stress to the robust scintillating plate. The image sensor has an improved ratio between the active, i.e. x-ray sensitive area and the total sensor area due to the replacement of standard wire connections at edges of the semiconductor detector (silicon detector) with vias and through-contacts thereby making it possible to reduce the dimensions of the printed circuit board below those of the semiconductor imager or detector and at the same time to increase the dimensions of the scintillating plate to conform to those of the semiconductor imager or detector. The mechanical integrity and robustness of the image sensor are improved due to the fact that the provision of vias and through-contacts makes it possible that the scintillating plate dominates the geometrical configuration of the sensor and at the same time provides a new dimension of mechanical integrity to the semiconductor imager or detector and printed circuit board which can now tightly be bonded to the scintillating plate. Even the replacement of the mechanically fragile "classical" wire bonds, bridging the edge of the semiconductor imager or detector down to the printed circuit board and insofar exposed to mechanical impacts and stress with embedded through-contacts results in improved mechanical properties and reliability of the image sensor.

Referring to FIG. 17 in conjunction with FIG. 18 and FIG. 19 an x-ray image sensor includes semiconductor imager or detector (silicon-die) 410 of basically rectangular shape, with two corners chamfered, a conventional printed circuit board 420, and a fiber optic plate 430 with a scintillator layer 440 on that surface which is opposite to the surface where the silicon-die 410 together with the printed circuit board 420 are bonded to the fiber optic plate 430. Both at the short edge of the rectangular left portion of the silicon die 410 and in the chamfered portions and at the remaining short edge in the right portion thereof, via 400, via 401, via 402 and via 403, respectively, and through-contacts are provided. At the bottom side of the silicon die 410, at the respective ends of the via, wire bonds 300 are provided for contacting the ends of the through-contacts to connecting points on the printed circuit board 420. It should be emphasized that this is just an exemplary connecting scheme. What also becomes apparent from the figures, are the specific geometrical relationships between the relevant plate-shaped elements, i.e. the fiber optic plate 430, the scintillator layer 440, the semiconductor detector 410 and the printed circuit board 420. Different from the conventional arrangement FIG. 14, FIG. 15 and FIG. 16 the dimensions of the printed circuit board, as compared to the semiconductor detector, are reduced and the dimensions of the fiber optic/scintillator plate are increased, to make the outer edges of the latter to be at least congruent with or slightly project over the semiconductor imager detector. As at the light receiving surface of the semiconductor detector there are no longer any wire bonds, the fiber optic plate 430 and the scintillator plate 440 can be made as large as to cover the full adjoining surface of the semiconductor detector and a full-surface tight bond (e.g. by means of a transparent adhesive) can be provided between them. This guarantees highest possible protection of the fragile semiconductor detector against mechanical impact or stress and high reliability even when the sensor is applied for dental purposes where movements, dropping, or accidental or desired biting on the sensor is likely to occur.

U.S. Pat. No. 7,615,414 teaches a method of fabricating a dental intraoral radiological image sensor with a fiber-optic plate. The method includes the steps for the collective production of a structure combining a semiconductor wafer, bearing a series of image detection circuits and a fiber-optic plate fixed to one face of the wafer. The semiconductor wafer is thinned in a step subsequent to the formation of the image detection circuits on the wafer and external access contact pads are produced on that face of the wafer which is not fixed to the fiber plate. The contact pads are for controlling the circuits and for receiving image signals coming from the sensor. The fiber-optic plate has a thickness such that it provides most of the mechanical integrity of the structure once the wafer has been thinned and to do so right to the end of the collective fabrication. The assembled structure consists of the wafer and the plate being subsequently diced into individual chips.

Referring to FIG. 20 in conjunction with FIG. 21 for a radiological image sensor, a scintillating structure is then deposited on the upper face of the fiber-optic plate (if the fibers themselves are not scintillating). The structure is formed by a cesium iodide scintillating layer 532 deposited on a thin carbon film 534. The assembly constitutes a flexible scintillating film 530 that is bonded on the cesium iodide side to the accessible face of the fiber-optic plate 520. At this stage the collective fabrication is complete and the plate structure bearing the integrated circuits formed in the semiconductor wafer 512 may be divided up into individual chips each of which corresponds to an individual image sensor. These chips are mounted on a support to which they are electrically connected. This support may be the base of a package or a printed circuit on a resin substrate or ceramic substrate bearing other components. The division into individual chips is performed by sawing the collective structure starting from only one face of this structure. An individual sensor chip is fixed to a support 540. The chip includes a superposed structure of a fiber-optic plate 520 and a semiconductor wafer element 512 (the plate bearing a scintillator 530 in the case of a radiological image sensor). The peripheral edges of the diced plate are superposed in exact coincidence with the peripheral edges of the semiconductor wafer because each side of the chip was cut by a single saw line, cutting both the plate and the thinned wafer. The chip is bonded via its rear face (the face bearing the semiconductor wafer and its conducting layer 526) to a first face of the support 540. It is slightly laterally offset from the support, and connection or bond wires 542 are bonded between the conducting pads, such as 528, and conducting areas 544 formed on the other face of the support 540. The fiber-optic plate 520 has a peripheral edge in exact coincidence with the peripheral edge of the semiconductor wafer 512 that remains. The scintillating structure 530 also has a peripheral edge in exact coincidence with the edge of the plate, since it was positioned during the collective fabrication before dicing. The sensor is intended to be illuminated by the x-rays arriving from the top. The photosensitive matrix on thinned semiconductor substrate is illuminated by the light from the scintillator via its front face side contrary to what occurs normally in the case of image sensors with a thinned substrate.

U.S. Pat. No. 8,829,444 teaches synthesis of advanced scintillators via vapor deposition techniques and transparent optical ceramic coating materials which have been fabricated from europium-doped lutetium oxide (Lu2O3:Eu) using physical vapor deposition and chemical vapor deposition techniques. The non-pixilated film coatings have columnar microcrystalline structure and excellent properties for use as radiological scintillators, namely very high density, high effective atomic number, and light output and emission wavelength suitable for use with silicon-based detectors having a very high quantum efficiency. The materials can be used in a multitude of high speed and high resolution imaging applications, including x-ray imaging in medicine.

Referring to FIG. 22 scintillator materials containing europium-doped lutetium oxide can be incorporated into a variety of devices, particularly optical devices designed to convert x-rays into visible light for quantification or imaging of an x-ray source, or for imaging of an object that scatters or absorbs x-rays. X-rays impinge on the device from the top of the figure (arrows). The scintillator material in the form of film 610 is adhered to a CCD device or layer 620. The thickness of the scintillator will depend on the application; however, the scintillator film should be sufficiently thick to absorb most of the incident x-rays to be imaged or quantified. The scintillator layer 610 can be in the range from about 50-500 microns in thickness, preferably about 200 microns thick. The thickness of CCD layer 620 can be, for example, about 350 microns. The CCD layer 620 can be supported by circuit substrate 630. The circuit substrate 630 can be any suitable material, but is a material such as FR4, a glass fiber-epoxy resin material used in printed circuit boards, which is electrically insulating and rigid. Optionally one or both faces of the device are encased in a layer of housing material 640 such as a plastic material or other material that is transparent to x-rays, at least on the side facing the incoming x-rays. A cable 650 connects the CCD layer 620 to a device such as a computer for input, analysis, display and storage of signals from the CCD, such as images. Devices containing the europium-doped lutetium oxide scintillator material can be used for any purpose related to detection of x-rays by scintillation. Such uses include recording dental x-rays; recording any type of medical x-rays such as in mammography, chest x-rays, or diagnostic x-rays; and recording images or performing analysis of any object that scatters or absorbs x-rays, including metals, microelectronics components and nanomaterials.

U.S. Pat. No. 9,223,034 teaches an x-ray imaging panel with thermally-sensitive adhesive for a laminated device which includes an extruded scintillation screen consisting of a scintillator material, a thermally-sensitive elastomer binder and a fiber optic plate. The thermally-sensitive elastomer binder is a thermoplastic polyolefin selected from the group consisting of high density polyethylene, low density polyethylene, medium density polyethylene, linear low density polyethylene, very low density polyethylene and combinations thereof. The scintillator material includes at least one phosphor selected from the group consisting of $Y_2SiO_5$:Cesium; $Y_2Si_2O_7$:Cesium; $LuAlO_3$:Ce; $Lu_2SiO_5$:Cesium; $Gd_2SiO_5$:Cesium; $YAlO_3$:Cesium; ZnO:Ga; $CdWO_4$; $LuPO_4$:Ce; PbWO; $Bi_4Ge_3O_{12}$; $CaWO_4$; $GdO_2S$:Tb, $GdO_2S$:Pr; $RE_3Al_5O_{12}$:Cesium and combinations thereof wherein RE is at least one rare earth metal.

Referring to FIG. 23 in conjunction with FIG. 24 a prior art intraoral x-ray imaging sensor 710 includes a housing, an electronic interface substrate 712 and a semiconductor imager 713. The housing has a rear (top) portion and a front (bottom) portion. The prior art intraoral x-ray imaging sensor 710 also includes a data cable 716 and a cable connector which mechanically couples the data cable 716 to the rear (top) portion of the housing and electrically couples the data cable 716 to the electronic interface substrate 712. The electronic interface substrate 712 has a first surface 719 and second surface 720 and is substantially rectangular with a mesial end 721 and a distal end 722. The electronic interface substrate 712 has a first cut corner and a second cut corner at its mesial end 721. The electronic interface substrate 712 may also have a third cut corner and a fourth cut corner at its distal end 722. The electronic interface substrate 712 is disposed within the housing 711. The semiconductor imager 713 has a first surface 723 and a second surface 724 and is substantially rectangular with a mesial end 725 and a distal end 726. The semiconductor imager 713 has a first cut corner and a second cut corner at its mesial end 725. The semiconductor imager 713 may also have a third cut corner and a fourth cut corner at its distal end 726. The semiconductor imager 713 consists of a silicon layer having an array of detector elements formed on its first surface 723 and its second surface 724 is disposed adjacent and contiguous to the first surface 719 of the electronic interface substrate 712. The semiconductor imager 713 may be either a CCD or a CMOS device and is mechanically and electrically coupled to the electronic interface substrate 712. The prior art intraoral x-ray imaging sensor 710 further includes a plurality of first electrical pads 727, a plurality of second electrical pads 728 and a plurality of bond-wires 729. The first electrical pads 733 are disposed on the first surface 719 of the electronic interface substrate 712. The second electrical pads 732 are disposed on the first surface 723 of the semiconductor imager 713. Each bond-wire 733 electrically couples one of the first electrical pads 731 to one of the second electrical pads 732. The first electrical pads 731 are disposed adjacent and contiguous to the mesial side 721 between the first cut corner and the second cut corner. The second electrical pads 732 are disposed adjacent and contiguous to the mesial side 725 between the first cut corner and the second cut corner. One of the bond-wires 733 mechanically and electrically couples each of the first electrical pads 731 to one of the second electrical pads 732. The prior art intraoral x-ray imaging sensor 710 further includes an x-ray converter layer 740 which has a first surface 741 and second surface 742. The x-ray converter layer 740 is substantially rectangular with a mesial end 743 and a distal end 744 and has a first cut corner and a second cut corner at its mesial end 743. The x-ray converter layer 740 may also have a third cut corner and a fourth cut corner at its distal end 744. The first surface 741 of the x-ray converter layer 740 is disposed adjacent to the first surface 723 of the semiconductor imager 713 within the housing. The x-ray converter layer 430 converts x-rays into photons to be received by the semiconductor imager 713 and the semiconductor imager 713 samples and detects the converted x-rays as electrical signals. The x-ray converter layer 740 includes a fiber optic plate 745 and a scintillating plate 746.

The inventor hereby incorporates the above-referenced patents and patent publication into his specification.

SUMMARY OF THE INVENTION

The present invention is an intraoral x-ray imaging sensor which includes housing, an electronic interface and a semiconductor imager. The housing has a top portion and bottom portion. The electronic interface substrate has a first surface and second surface and is substantially rectangular with a mesial end and a distal end. The electronic interface substrate has a first cut corner and a second cut corner at either its mesial end or its distal end. The electronic interface substrate is disposed within the housing. The semiconductor imager has a first surface and a second surface and is substantially rectangular with a mesial end and a distal end. The semiconductor imager has a first cut corner and a second cut corner at either its mesial end or its distal end. The semiconductor imager consists of a silicon layer having an array of detector elements formed on its first surface and its second surface is disposed adjacent and contiguous to the first surface of the electronic interface substrate. The semiconductor imager may be either a CCD or a CMOS device and is mechanically and electrically coupled to the electronic interface substrate. The intraoral x-ray imaging sensor also includes a plurality of first electrical pads, a plurality of second electrical pads and a plurality of bond wires. The first electrical pads are disposed on the first surface of the electronic interface substrate. The second electrical pads are disposed on the first surface of the semiconductor imager. Each bond wire electrically couples one of the first electrical pads to one of the second electrical pads.

In a first aspect of the present invention some of the first electrical pads are disposed adjacent and contiguous to the first cut corner and the remainder of the first electrical pads are disposed adjacent and contiguous to the second cut corner and some of the of second electrical pads are disposed adjacent and contiguous to the first cut corner and the remainder of the second electrical pads are disposed adjacent and contiguous to the second cut corner.

In a second aspect of the present invention the intraoral x-ray imaging sensor includes an x-ray converter layer which has a first surface and second surface and is substantially rectangular with a distal end having a first cut corner and a second cut corner and a mesial end. The first surface of the x-ray converter layer is disposed adjacent to the first surface of the semiconductor imager within the housing. The x-ray converter layer converts x-rays into photons to be received by the semiconductor imager and the semiconductor imager samples and detects the converted x-rays as electrical signals.

In a third aspect of the present invention the intraoral x-ray imaging sensor includes a data cable which is mechanically coupled to the top portion of the housing and electrically coupled to the electronic interface substrate.

In a fourth aspect of the present invention the intraoral x-ray imaging sensor includes a wireless transmitter which is mechanically and electrically coupled to the electronic interface substrate.

In a fifth aspect of the present invention the housing is formed by being encapsulated in an epoxy resin.

In a sixth aspect of the present invention the electronic interface substrate and the semiconductor imager are geometrically similar.

In a seventh aspect of the present invention the electronic interface substrate has circuitry which includes a processor, a read only memory, a random access memory and an input/output module and is disposed on its second surface.

In an eighth aspect of the present invention dead space in either its mesial end or its distal end is to be minimized thereby representing a significant advance over the prior art dental radiological image sensors and not only allowing dental practitioners to obtain much better radiographs of all teeth being radiographed, but also adding the patient comfort.

In a ninth aspect of the present invention the dental radiological image sensors are intended to be accommodated in areas where available space is reduced, and for which the aim, nevertheless, is to have an image capture area that is as large as possible.

In a tenth aspect of the present invention the dental radiological image sensors are intended to be accommodated in the mouth of a patient and the size of the image taken must correspond at least to the height of a tooth and the width of several teeth. Since the space constraints are therefore considerable it is necessary to try to save as much as possible with regard to the volume of the sensor with a given image surface while addressing the need for the patient's comfort thereby entailing additional ergonomic constraints.

In an eleventh aspect of the present invention the dental radiological image sensors minimizes the dead space by placing the first and second electrical pads and the wire bonds in the cut corners.

Other aspects and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
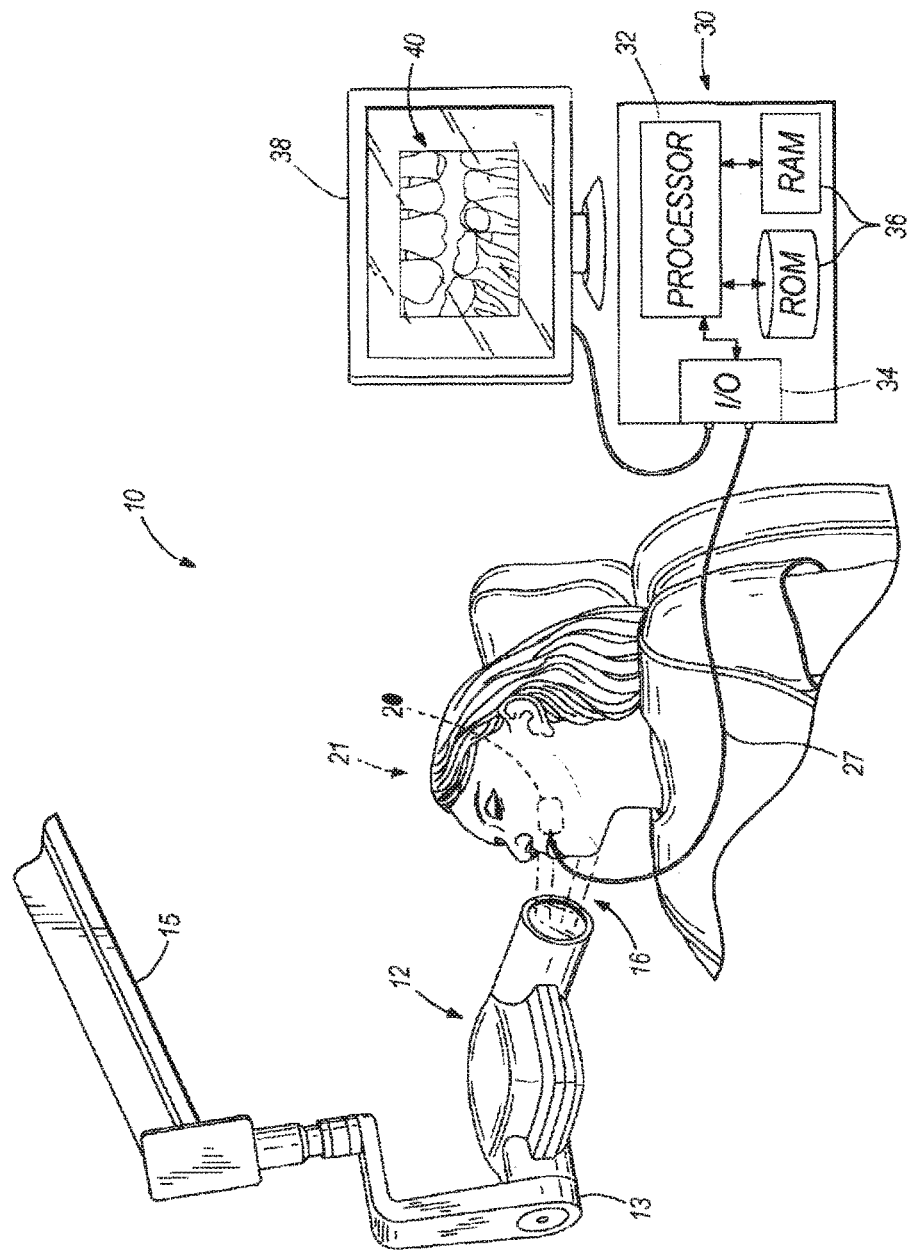
FIG. 1 is a schematic diagram of a dental x-ray system including an x-ray source, an intraoral sensor located in a patient's mouth and a computer connected to the intraoral sensor in accordance with U.S. Pat. No. 9,259,197.
Figure 2:
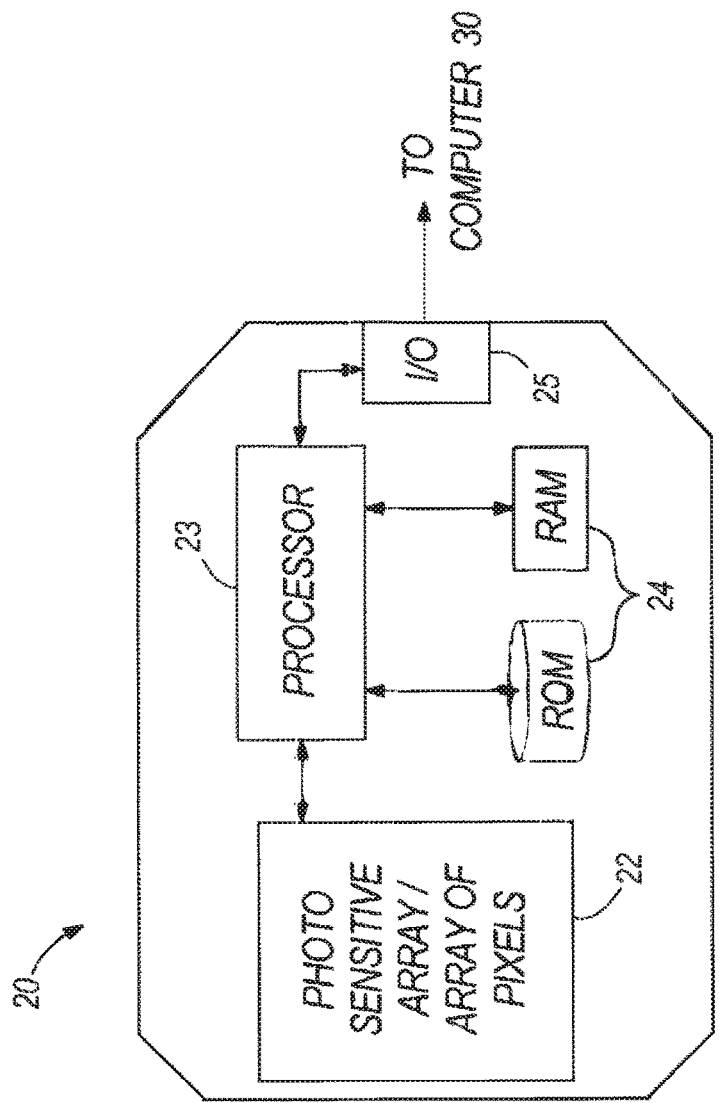
FIG. 2 is a schematic diagram of the intraoral sensor of FIG. 1 showing internal components of the sensor.
Figure 3:
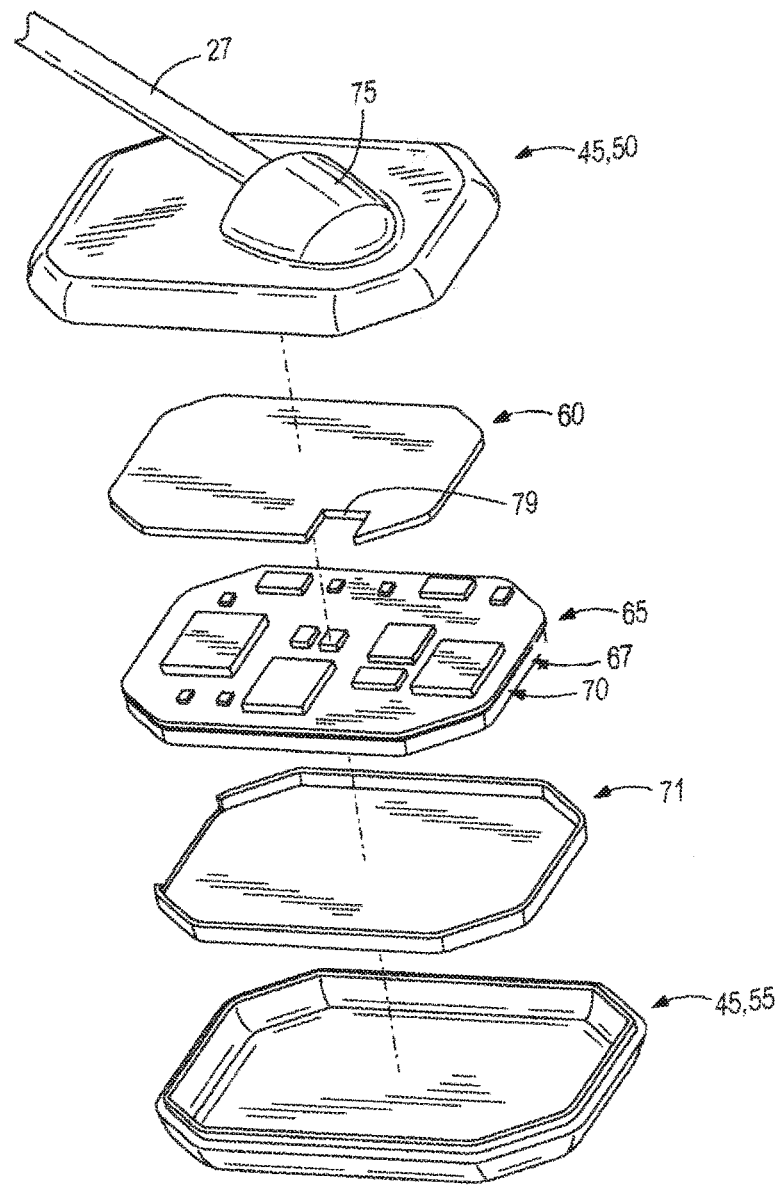
FIG. 3 is an exploded perspective drawing of the intraoral sensor of FIG. 1.
Figure 4:
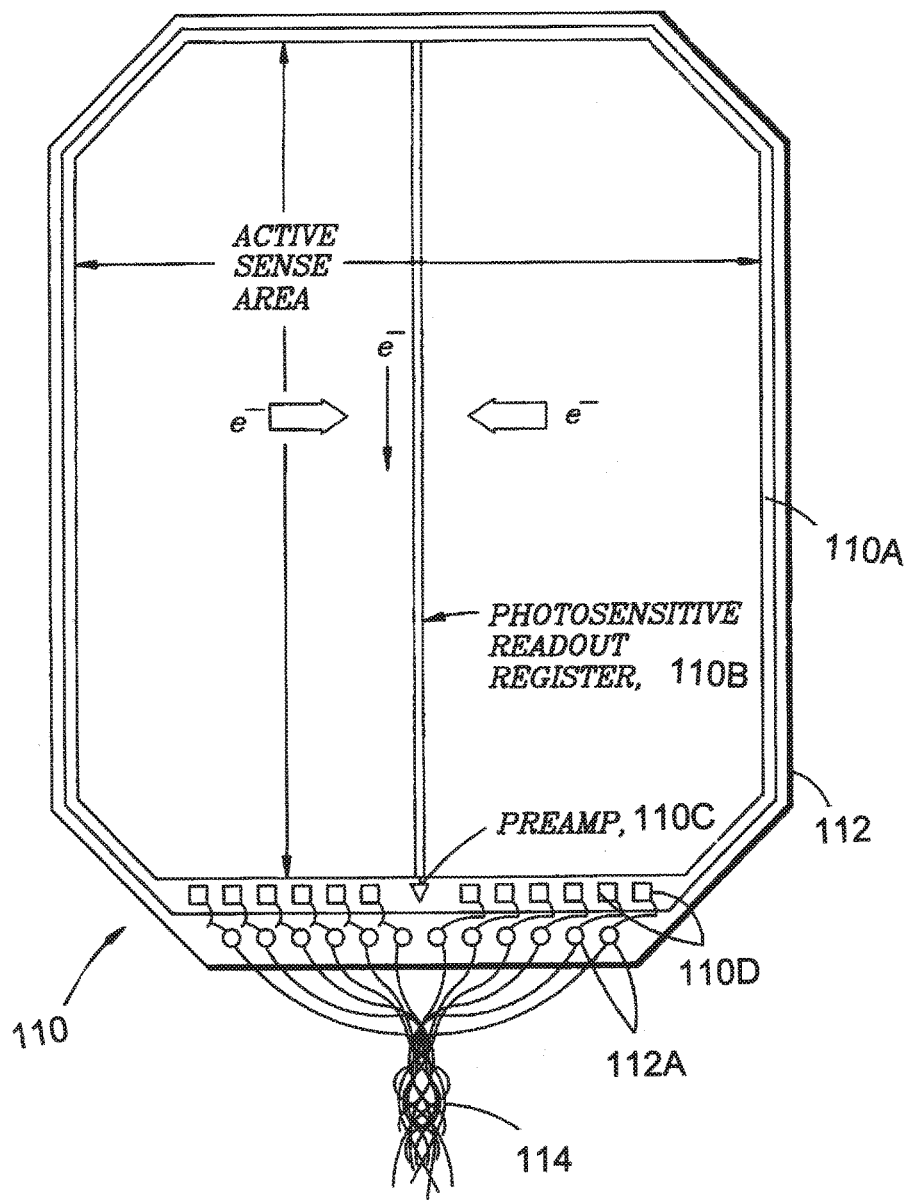
FIG. 4 is an enlarged plan view of a CCD radiation sensor array in accordance U.S. Pat. No. 5,510,623.
Figure 5:
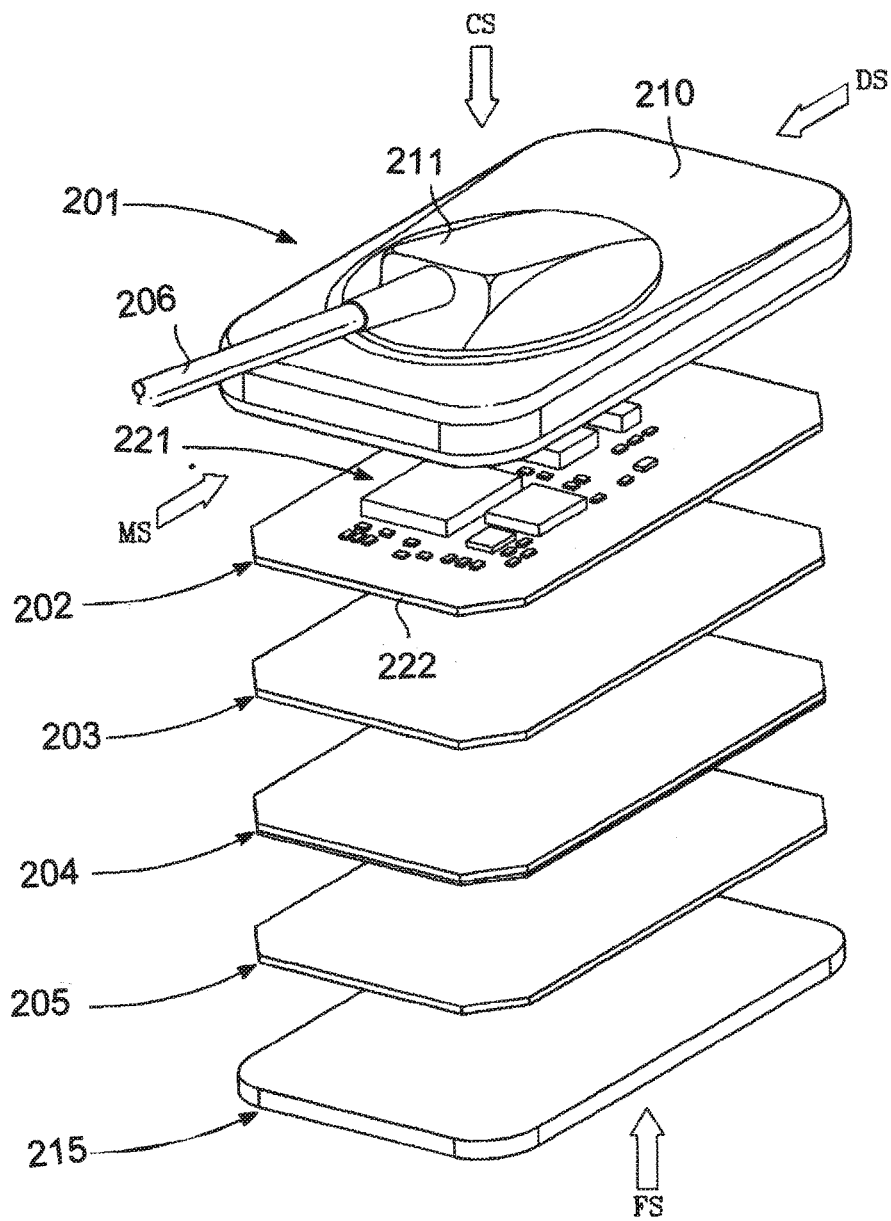
FIG. 5 is an exploded perspective drawing of a prior art radiological image sensor and its primary components as disclosed in U.S. Patent Publication No. 2014/0023177.
Figure 6:
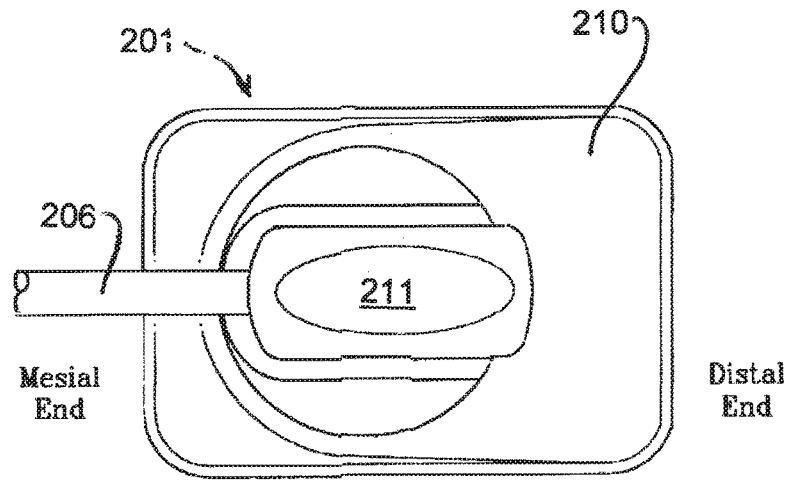
FIG. 6 is a top plan view of the prior art radiological image sensor of FIG. 5 showing the orientation between distal and mesial.
Figure 7:
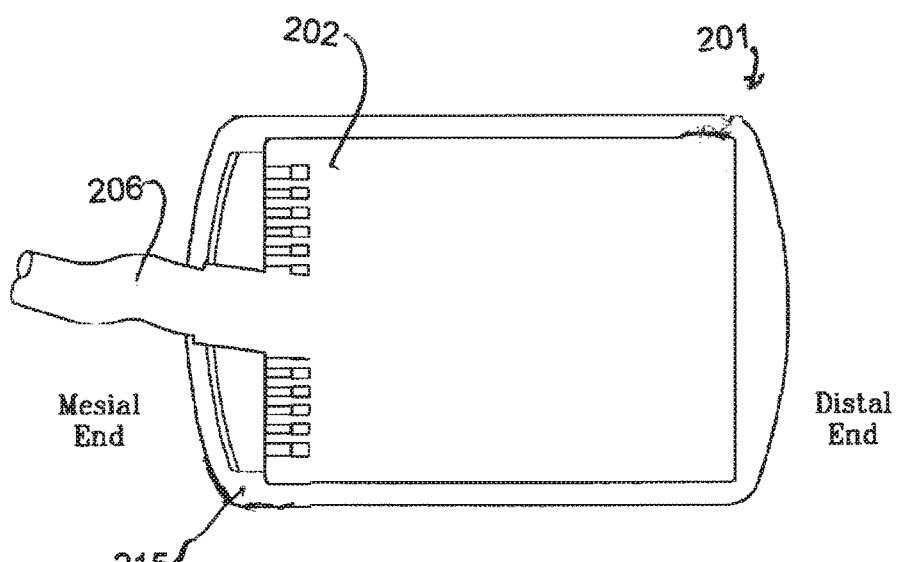
FIG. 7 is a top plan view of the prior art radiological image sensor of FIG. 5 illustrating the dead space on the mesial end of a typical traditional sensor.
Figure 8:
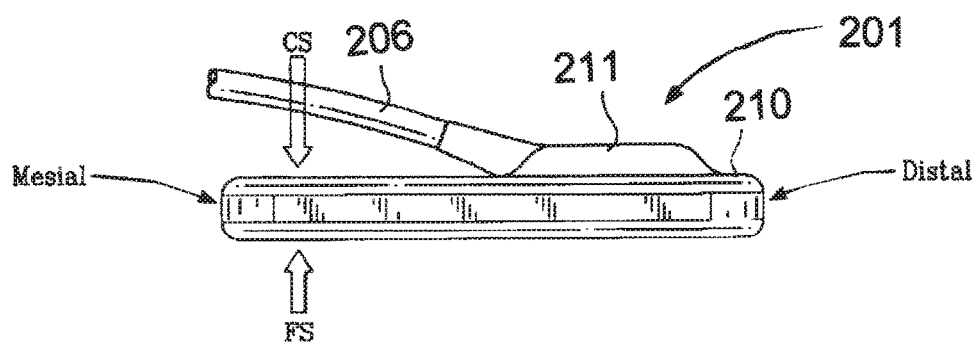
FIG. 8 is a side view of a radiological image sensor showing a cable button connector located more proximate its distal side than its mesial side according to U.S. Patent Publication No. 2014/0023177.
Figure 9:
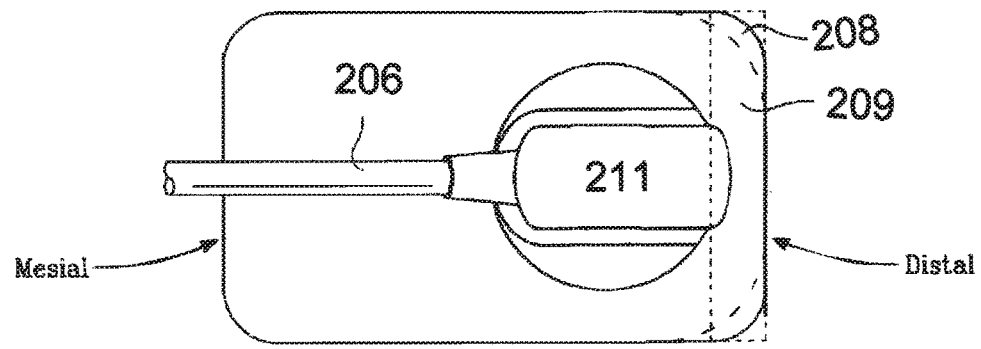
FIG. 9 is a top view cutaway of the radiological image sensor of FIG. 8 showing the dead space located at the distal end of the radiological image sensor.
Figure 10:
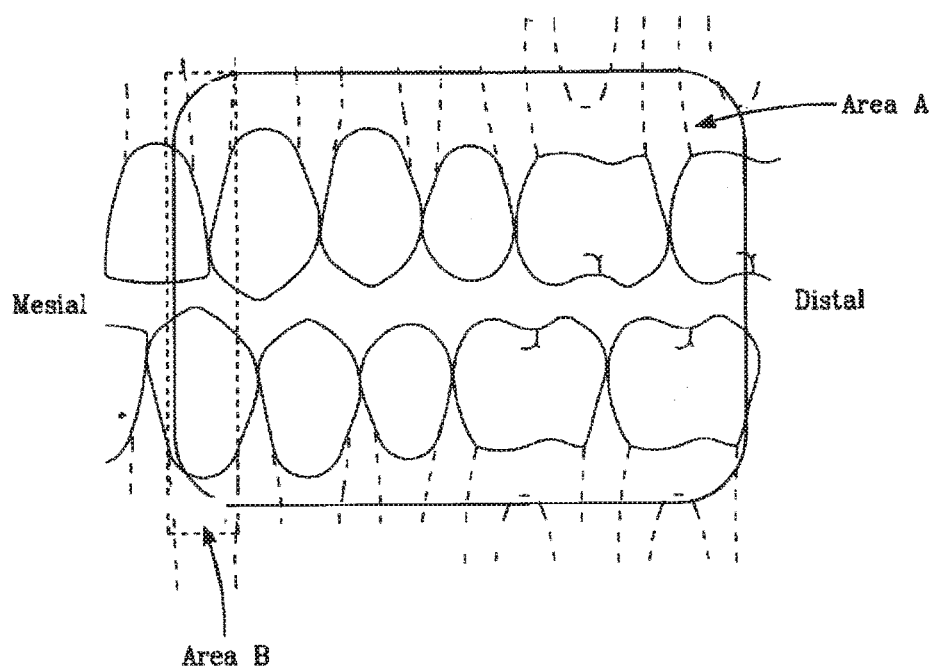
FIG. 10 is a schematic drawing illustrating typical loss of imaging area due to dead space for sensor electronics for a typical digital sensor.
Figure 11:
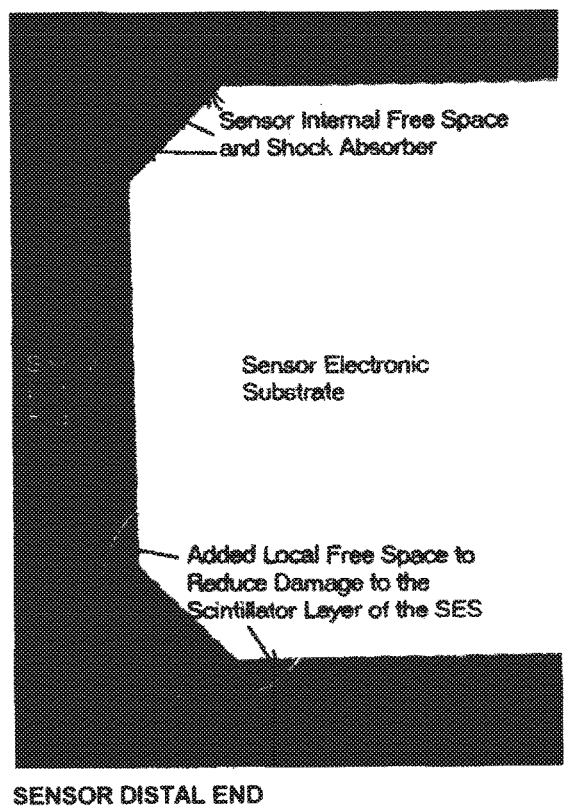
FIG. 11 and FIG. 12 illustrate sensor internal free space and shock absorber area in a radiological image sensor.
Figure 12:
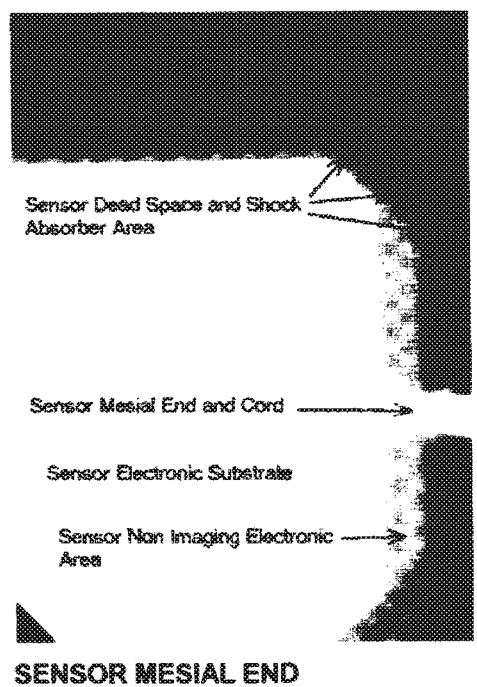
Figure 13:
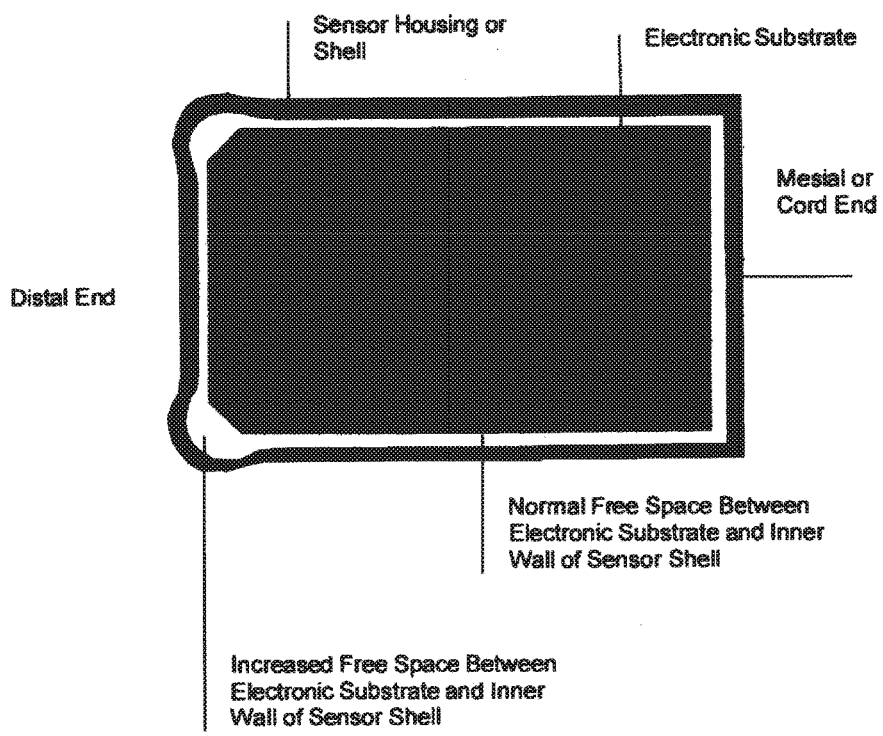
FIG. 13 illustrates an improvement of a sensor in accordance with U.S. Patent Publication No. 2014/0023177.
Figure 14:
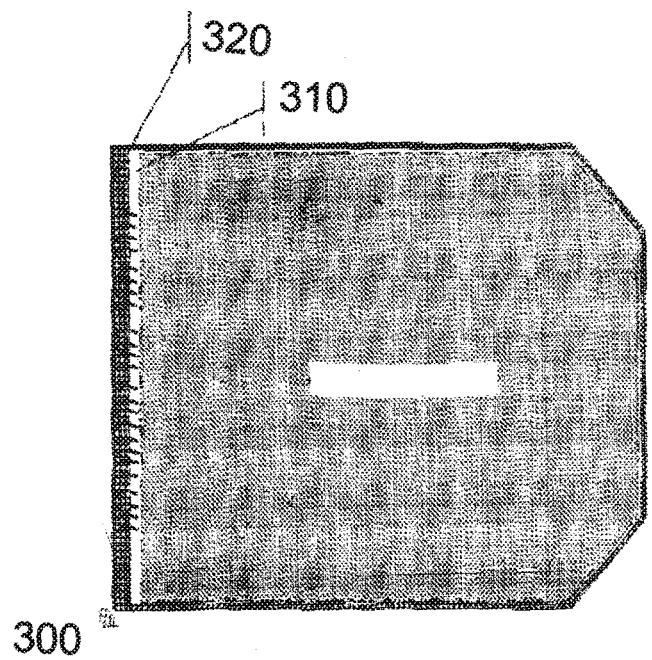
FIG. 14 is a top plan view of a prior art plate-shaped x-ray image sensor as disclosed in U.S. Patent Publication No. 2014/0367578.
Figure 15:
FIG. 15 is a side view of a semiconductor detector and a PCB of the plate-shaped x-ray image sensor of FIG. 14.
Figure 16:
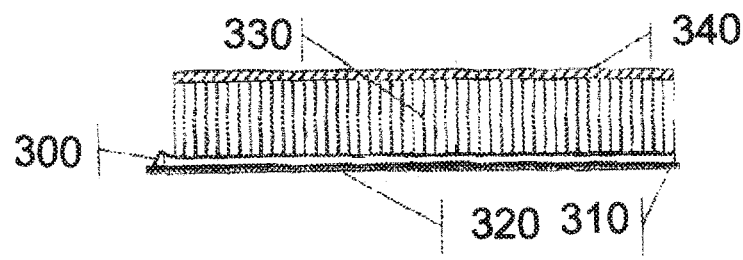
FIG. 16 is a side-view of the semiconductor detector and the PCB of the plate-shaped x-ray image sensor of FIG. 14 with the addition of a scintillating plate including a fiber optic plate and a scintillating layer located on the top towards the x-ray source of the fiber optic plate.
Figure 17:
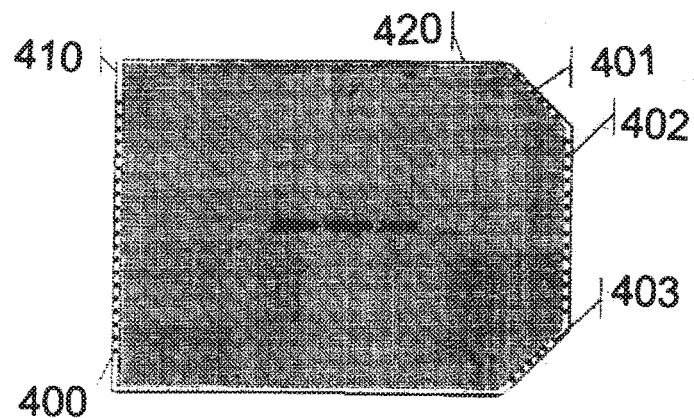
FIG. 17 is a top plan view of a plate-shaped x-ray image sensor in accordance with U.S. Patent Publication No. 2014/0367578.
Figure 18:
FIG. 18 is a side view of a semiconductor detector and a PCB of the plate-shaped x-ray image sensor of FIG. 14.
Figure 19:
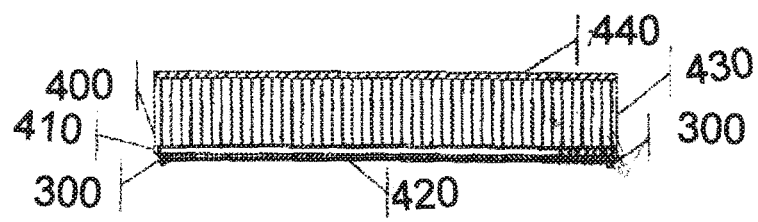
FIG. 19 is a side-view of the semiconductor detector and the PCB of the plate-shaped x-ray image sensor of FIG. 14 with the addition of a scintillating plate including a fiber optic plate and a scintillating layer located on the top towards the x-ray source of the fiber optic plate.
Figure 20:
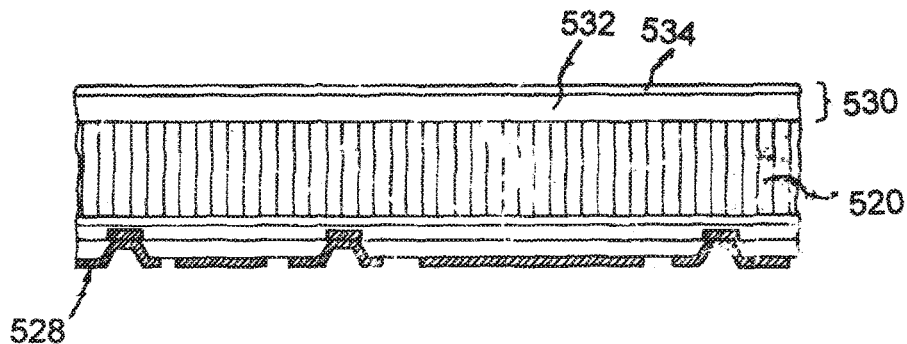
FIG. 20 is a side view illustrating the deposition of a scintillator on the accessible face of the fiber-optic plate in accordance with U.S. Pat. No. 7,615,414.
Figure 21:
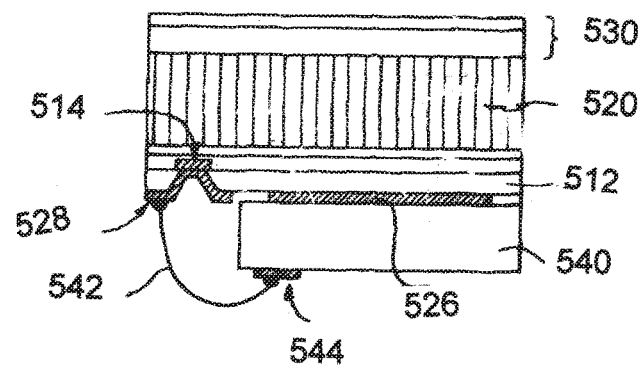
FIG. 21 is a side view of a completed radiological image sensor plate in accordance with U.S. Pat. No. 7,615,414 wherein the completed radiological image sensor plate includes a wafer/plate structure diced into an individual chip mounted on a support to which it is connected by wire-bonded wires.
Figure 22:
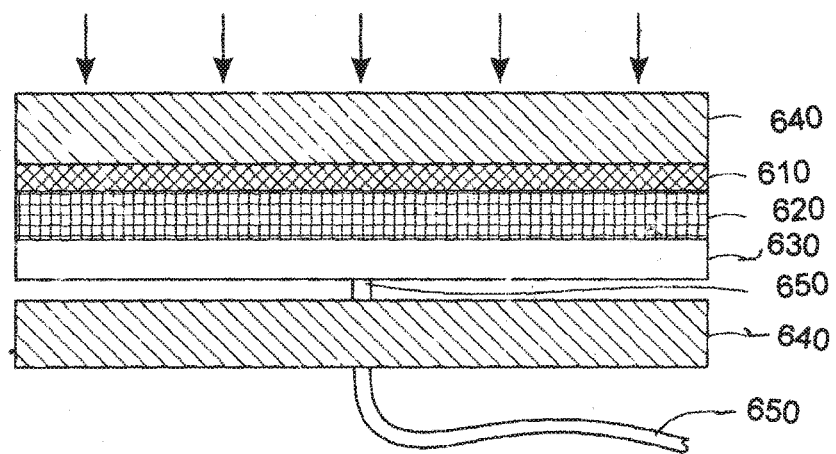
FIG. 22 is schematic drawing of an x-ray imaging device for dentistry featuring a Lu2O3:Eu scintillator film in accordance with U.S. Pat. No. 8,829,444.
Figure 24:
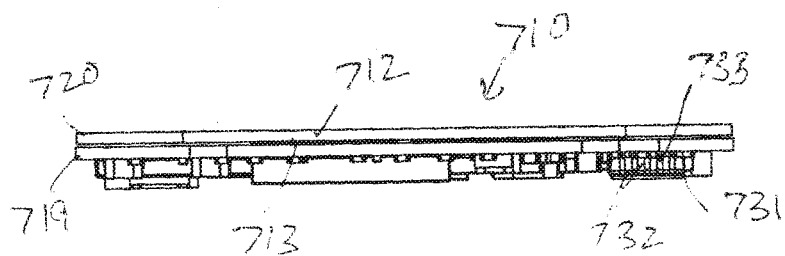
FIG. 24 is a side view of the prior art radiographic imaging sensor of FIG. 23.
Figure 23:
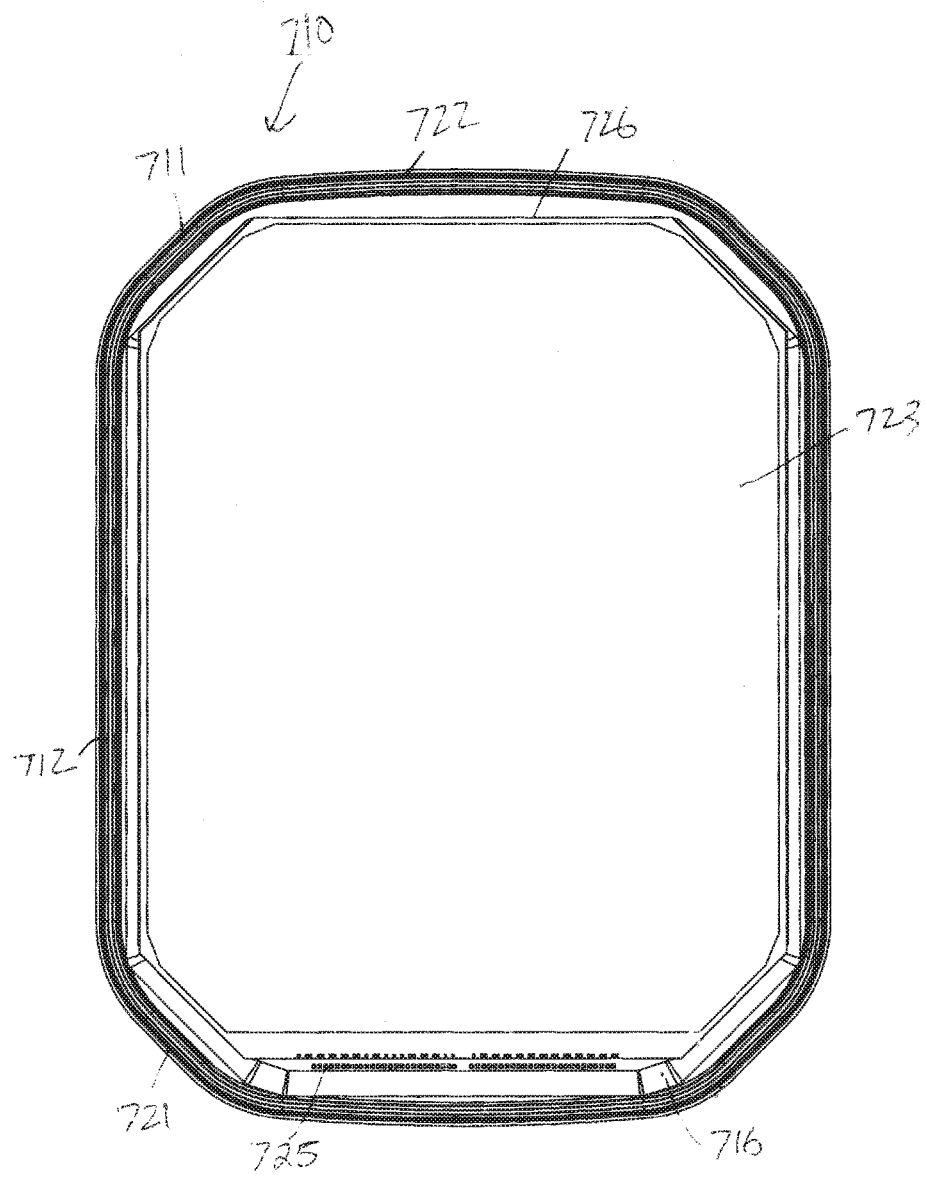
FIG. 23 is a top plan view of prior art radiographic imaging sensor.
Figure 25:
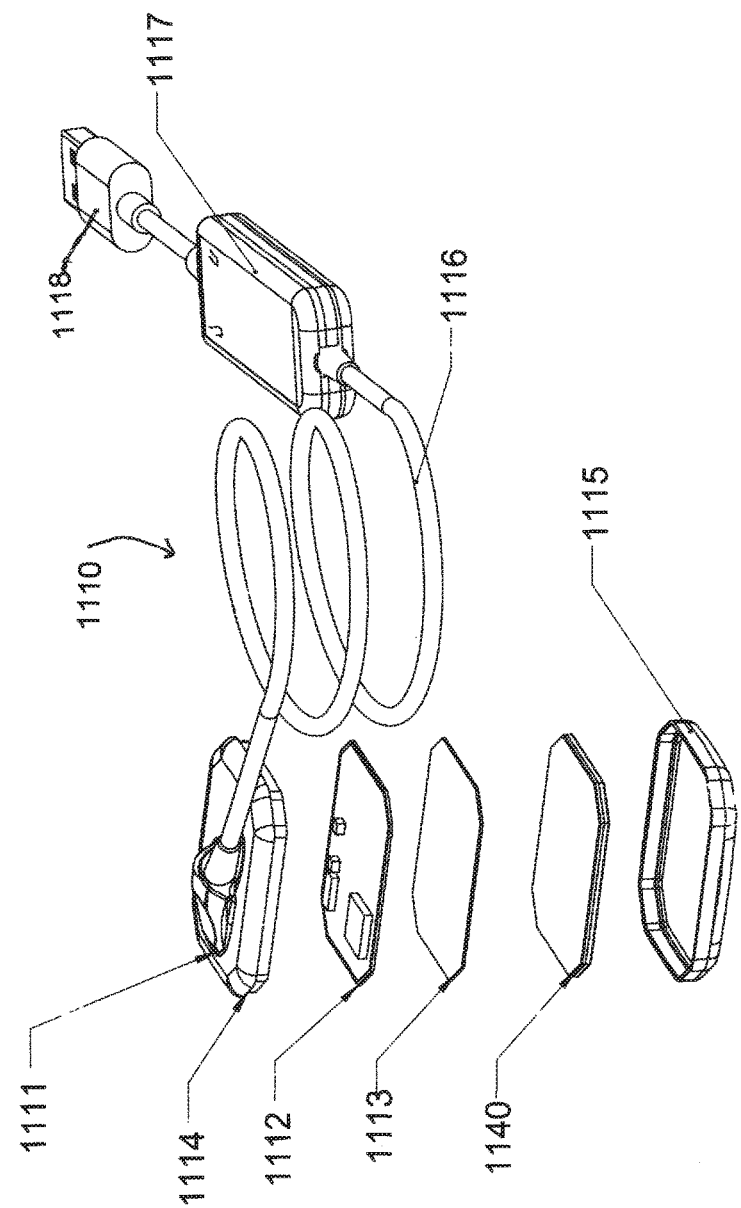
FIG. 25 is an exploded perspective view showing assembly view of a first intraoral x-ray imaging sensor and its primary components according to the first embodiment of the present invention.

Referring to FIG. 25 a first intraoral x-ray imaging sensor 1110 includes a housing 1111, an electronic interface substrate 1112 and a semiconductor imager 1113. The housing 1111 has a rear (top) portion 1114 and a front (bottom) portion 1115. The first intraoral x-ray imaging sensor 1110 also includes a data cable 1116 and a cable connector 1117 which mechanically couples the data cable 1116 to the top portion 1114 of the housing 1111 and electrically couples the data cable 1116 to the electronic interface substrate 1112. The data cable 1116 may be a USB cable with a USB connector 1118. The first intraoral x-ray imaging sensor 1110 may alternatively include a wireless transmitter which is mechanically and electrically coupled to the electronic interface substrate 1112.

Figure 26:
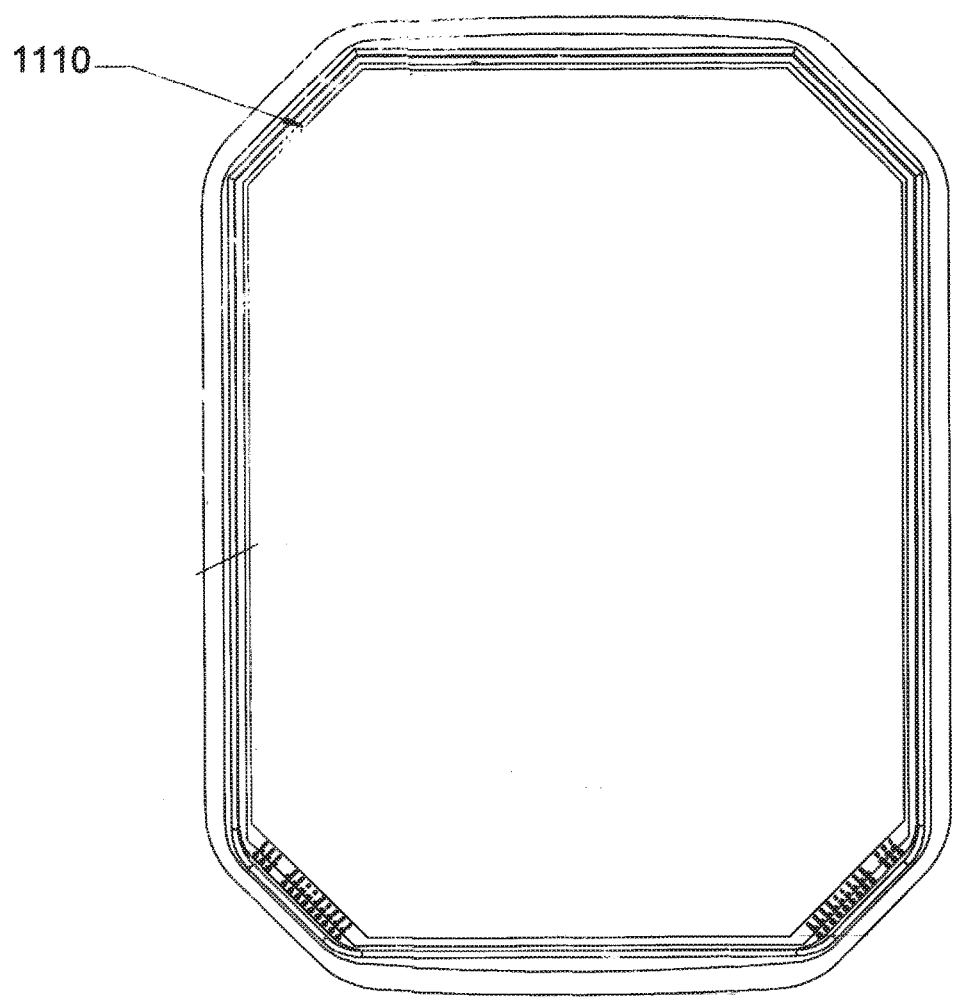
FIG. 26 is a top plan view of the first intraoral x-ray imaging sensor of FIG. 25.

Referring to FIG. 26 in conjunction with FIG. 25 the electronic interface substrate 1112 has a first surface 1119 and second surface 1120 and is substantially rectangular with a mesial end 1121 and a distal end 1122. The electronic interface substrate 1112 has a first cut corner and a second cut corner at its mesial end 1121. The electronic interface substrate 1112 may also have a third cut corner and a fourth cut corner at its distal end 1122. The electronic interface substrate 1112 is disposed within the housing 1111. The semiconductor imager 1113 has a first surface 1123 and a second surface 1124 and is substantially rectangular with a mesial end 1125 and a distal end 1126. The semiconductor imager 1113 has a first cut corner and a second cut corner at its mesial end 1125. The semiconductor imager 1113 may also have a third cut corner and a fourth cut corner at its distal end 1126.

Figure 27:
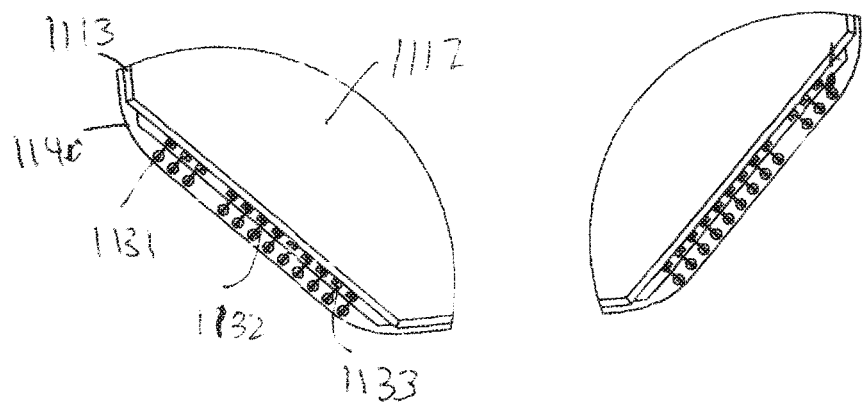
FIG. 27 is a side view of the first intraoral x-ray imaging sensor of FIG. 25.

Referring to FIG. 27 in conjunction with FIG. 25 and FIG. 26 the semiconductor imager 1113 consists of a silicon layer having an array of detector elements formed on its first surface 1123 and its second surface 1124 is disposed adjacent and contiguous to the first surface 1119 of the electronic interface substrate 1112. The semiconductor imager 1113 may be either a CCD or a CMOS device and is mechanically and electrically coupled to the electronic interface substrate 1112.

Referring to FIG. 26 in conjunction with FIG. 25 and FIG. 27 the first intraoral x-ray imaging sensor 1110 further includes a plurality of first electrical pads 1131, a plurality of second electrical pads 1132 and a plurality of bond-wires 1133. The first electrical pads 1131 are disposed on the first surface 1121 of the electronic interface substrate 1112. The second electrical pads 1132 are disposed on the first surface 1127 of the semiconductor imager 1113. Each bond-wire 1133 electrically couples one of the first electrical pads 1131 to one of the second electrical pads 1132. Some of the first electrical pads 1131 are disposed adjacent and contiguous to the first cut corner and the remainder of the first electrical pads 1131 are disposed adjacent and contiguous to the second cut corner. Some of the of second electrical pads 1132 are disposed adjacent and contiguous to the first cut corner and the remainder of the second electrical pads 1132 are disposed adjacent and contiguous to the second cut corner.

Figure 28:
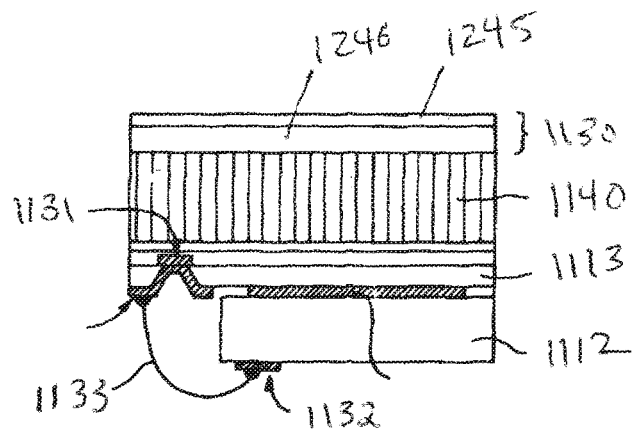
FIG. 28 is a side view of the first intraoral x-ray imaging sensor of FIG. 25 showing one of the first electrical pads, one of the second electrical pads and one of the bond-wires coupling each of the first electrical pads to one of the second electrical pads.

Referring to FIG. 28 in conjunction with FIG. 26 and FIG. 27 one of the bond-wires 1133 mechanically and electrically couples each of the first electrical pads 1131 to one of the second electrical pads 1132.

Referring to FIG. 28 in conjunction with FIG. 25, FIG. 26 and FIG. 27 the first intraoral x-ray imaging sensor 1110 still further includes an x-ray converter layer 1140 which has a first surface 1141 and second surface 1142. The x-ray converter layer 1140 is substantially rectangular with a mesial end 1143 and a distal end 1144 and has a first cut corner and a second cut corner at its mesial end 1143. The x-ray converter layer 1140 may also have a third cut corner and a fourth cut corner at its distal end 1144. The first surface 1141 of the x-ray converter layer 1140 is disposed adjacent to the first surface 1125 of the semiconductor imager 1113 within the housing 1111. The x-ray converter layer 1140 converts x-rays into photons to be received by the semiconductor imager 1113 and the semiconductor imager 1113 samples and detects the converted x-rays as electrical signals. The x-ray converter layer 1140 includes a fiber optic plate 1145 and a scintillating plate 1146.

Referring to FIG. 26 in conjunction with FIG. 27 the electronic interface substrate 1112 and the semiconductor imager 1113 are geometrically similar. The electronic interface substrate 1112 is slightly larger than the semiconductor imager 1113. They are basically congruent. The x-ray converter layer 1140 and the semiconductor imager 1113 are geometrically similar. The x-ray converter layer 1140 is slightly larger than the semiconductor imager 1113 and arranged such that none of the edges of the semiconductor imager 1113 projects over a corresponding edge of the x-ray converter layer 1140.

Figure 29:
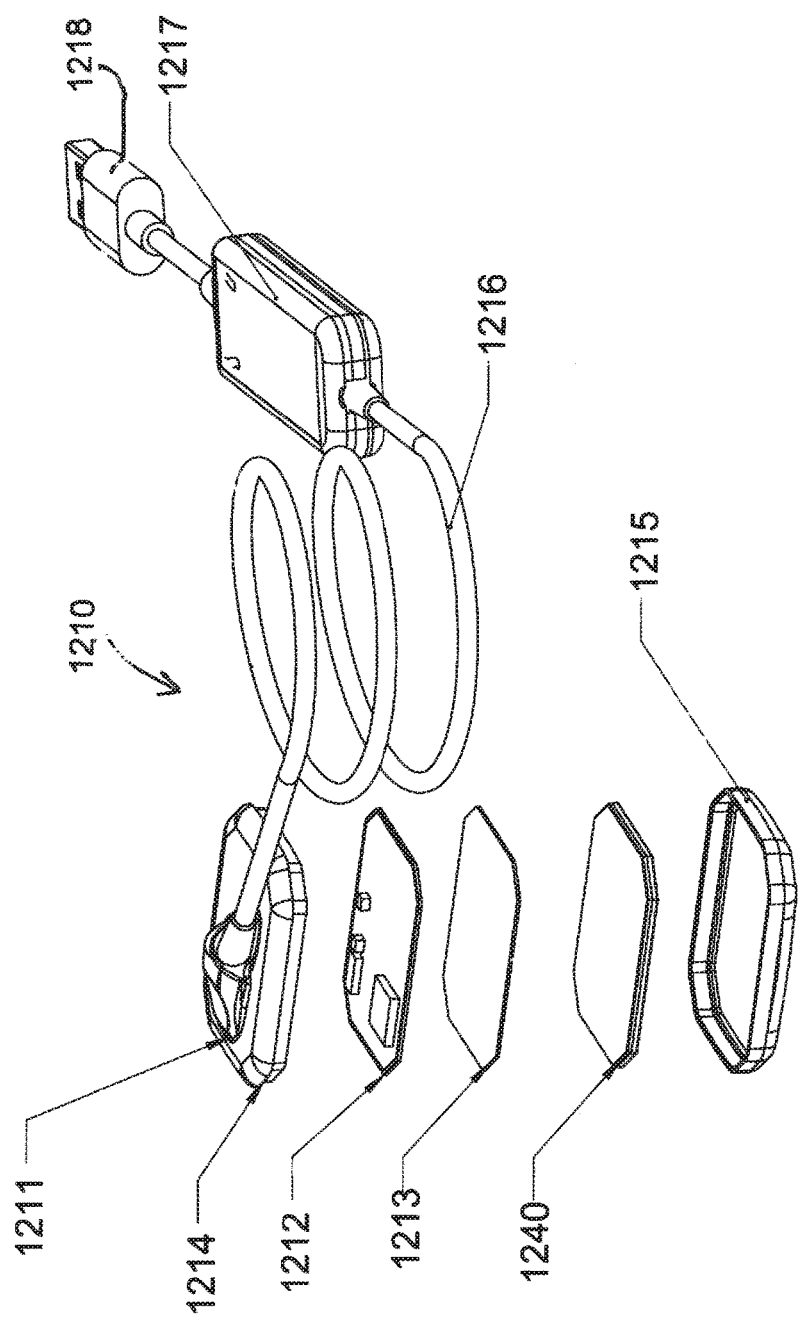
FIG. 29 is an exploded perspective view showing assembly view of a second intraoral x-ray imaging sensor and its primary components according to the second embodiment of the present invention.

Referring to FIG. 29 a first intraoral x-ray imaging sensor 1210 includes a housing 1211, an electronic interface substrate 1212 and a semiconductor imager 1213. The housing 1211 has a rear (top) portion 1214 and a front (bottom) portion 1215. The first intraoral x-ray imaging sensor 1210 also includes a data cable 1216 and a cable connector 1217 which mechanically couples the data cable 1216 to the rear (top) portion 1214 of the housing 1211 and electrically couples the data cable 1216 to the electronic interface substrate 1212. The data cable 1216 may be a USB cable with a USB connector 1218. The first intraoral x-ray imaging sensor 1210 may alternatively include a wireless transmitter which is mechanically and electrically coupled to the electronic interface substrate 1212.

Figure 30:
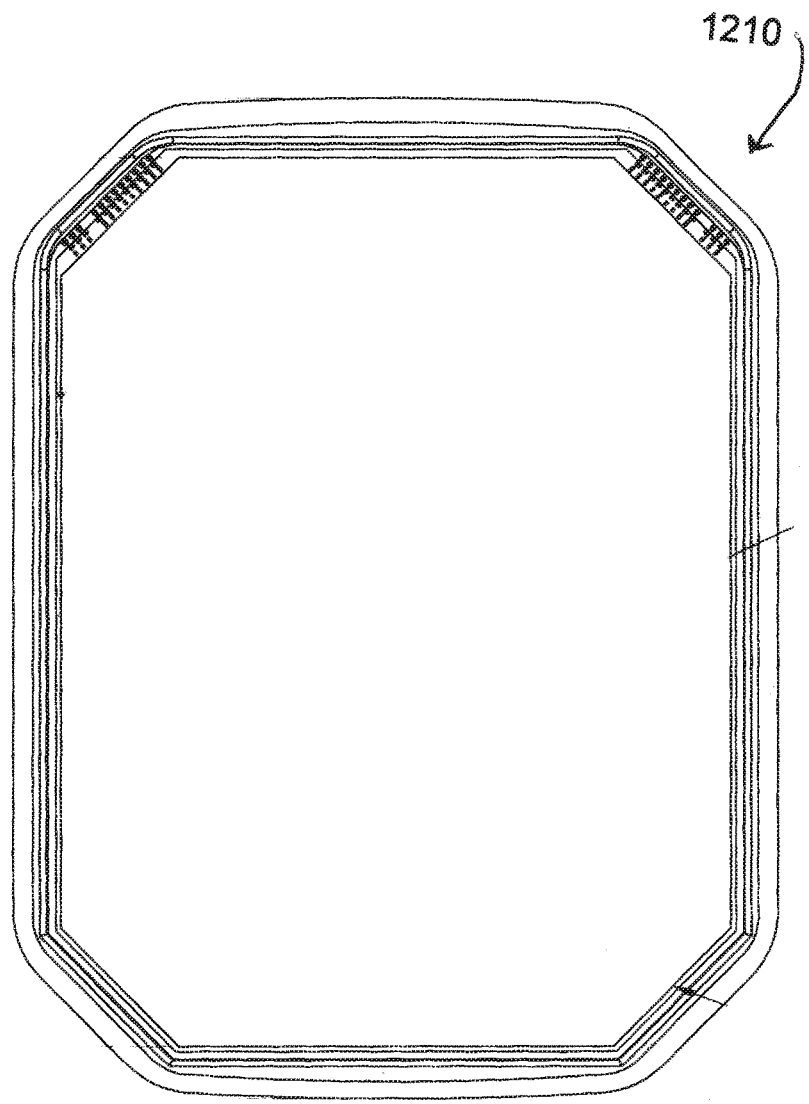
FIG. 30 is a top plan view of the second intraoral x-ray imaging sensor of FIG. 29.

Referring to FIG. 30 in conjunction with FIG. 29 the electronic interface substrate 1212 has a first surface 1219 and second surface 1220 and is substantially rectangular with a mesial end 1221 and a distal end 1222. The electronic interface substrate 1212 has a first cut corner and a second cut corner at its mesial end 1221. The electronic interface substrate 1212 may also have a third cut corner and a fourth cut corner at its distal end 1222. The electronic interface substrate 1212 is disposed within the housing 1211. The semiconductor imager 1213 has a first surface 1223 and a second surface 1224 and is substantially rectangular with a mesial end 1225 and a distal end 1226. The semiconductor imager 1213 has a first cut corner and a second cut corner at its mesial end 1225. The semiconductor imager 1213 may also have a third cut corner and a fourth cut corner at its distal end 1226.

Figure 31:
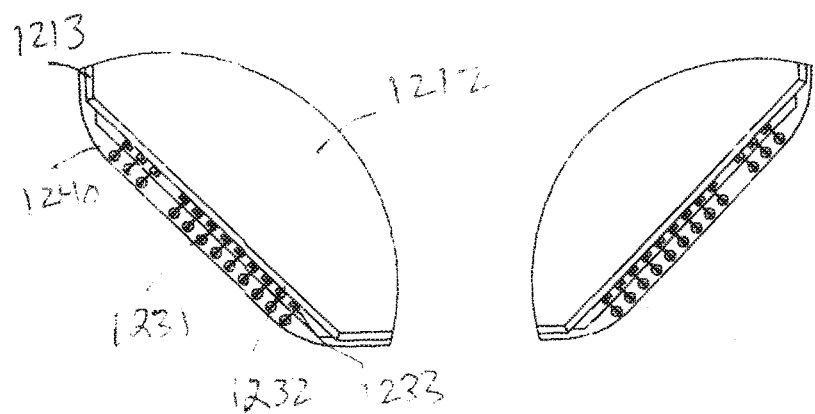
FIG. 31 is a side view of the second intraoral x-ray imaging sensor of FIG. 29.

Referring to FIG. 31 in conjunction with FIG. 29 and FIG. 30 the semiconductor imager 1213 consists of a silicon layer having an array of detector elements formed on its first surface 1223 and its second surface 1224 is disposed adjacent and contiguous to the first surface 1219 of the electronic interface substrate 1212. The semiconductor imager 1213 may be either a CCD or a CMOS device and is mechanically and electrically coupled to the electronic interface substrate 1212.

Referring to FIG. 30 in conjunction with FIG. 29 and FIG. 31 the first intraoral x-ray imaging sensor 1210 further includes a plurality of first electrical pads 1231, a plurality of second electrical pads 1232 and a plurality of bond-wires 1233. The first electrical pads 1231 are disposed on the first surface 1221 of the electronic interface substrate 1212. The second electrical pads 1232 are disposed on the first surface 1227 of the semiconductor imager 1213. Each bond-wire 1233 electrically couples one of the first electrical pads 1231 to one of the second electrical pads 1232. Some of the first electrical pads 1231 are disposed adjacent and contiguous to the first cut corner and the remainder of the first electrical pads 1231 are disposed adjacent and contiguous to the second cut corner. Some of the of second electrical pads 1232 are disposed adjacent and contiguous to the first cut corner and the remainder of the second electrical pads 1232 are disposed adjacent and contiguous to the second cut corner.

Figure 32:
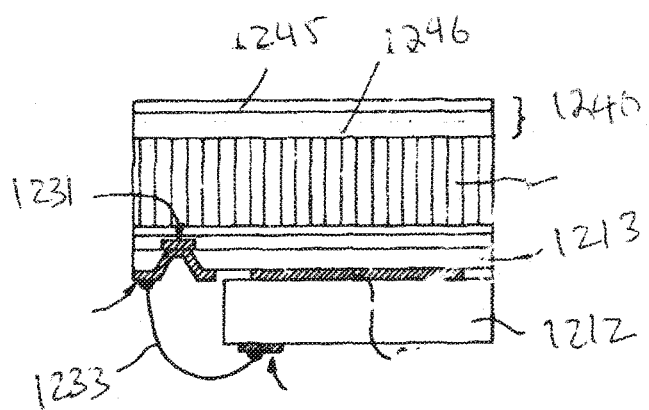
FIG. 32 is a side view of the second intraoral x-ray imaging sensor of FIG. 29 showing one of the first electrical pads, one of the second electrical pads and one of the bond-wires coupling each of the first electrical pads to one of the second electrical pads.

Referring to FIG. 32 in conjunction with FIG. 30 and FIG. 31 one of the bond-wires 1233 mechanically and electrically couples each of the first electrical pads 1231 to one of the second electrical pads 1232.

Referring to FIG. 32 in conjunction with FIG. 29, FIG. 30 and FIG. 31 the first intraoral x-ray imaging sensor 1210 still further includes an x-ray converter layer 1240 which has a first surface 1241 and second surface 1242. The x-ray converter layer 1240 is substantially rectangular with a mesial end 1243 and a distal end 1244 and has a first cut corner and a second cut corner at its mesial end 1243. The x-ray converter layer 1240 may also have a third cut corner and a fourth cut corner at its distal end 1244. The first surface 1241 of the x-ray converter layer 1240 is disposed adjacent to the first surface 1225 of the semiconductor imager 1213 within the housing 1211. The x-ray converter layer 1240 converts x-rays into photons to be received by the semiconductor imager 1213 and the semiconductor imager 1213 samples and detects the converted x-rays as electrical signals. The x-ray converter layer 1240 includes a fiber optic plate 1245 and a scintillating plate 1246.

Referring to FIG. 30 in conjunction with FIG. 31 the electronic interface substrate 1212 and the semiconductor imager 1213 are geometrically similar. The electronic interface substrate 1212 is slightly larger than the semiconductor imager 1213. They are basically congruent. The x-ray converter layer 1240 and the semiconductor imager 1213 are geometrically similar. The x-ray converter layer 1240 is slightly larger than the semiconductor imager 1213 and arranged such that none of the edges of the semiconductor imager 1213 projects over a corresponding edge of the x-ray converter layer 1240.

From the foregoing an intraoral x-ray imaging sensor 9 which not only decreases dead space, but also increases a patient's comfort has been described.

Accordingly, it is intended that the foregoing disclosure and showing made in the drawing shall be considered only as an illustration of the principle of the present invention.

What is claimed is:

1. An intraoral x-ray imaging sensor comprising:
   a. an electronic interface substrate wherein said electronic interface substrate has a first surface and a second surface and is substantially rectangular with a mesial end and a distal end wherein said electronic interface substrate has a first cut corner and a second cut corner at its said distal end;
   b. a semiconductor imager mechanically and electrically coupled to said electronic interface substrate wherein said semiconductor imager has a first surface and a second surface and consists of a silicon layer having an array of detector elements formed on its said first surface and is substantially rectangular with a mesial end and a distal end wherein said semiconductor imager has a first cut corner and a second cut corner at its said distal end and wherein said second surface of said semiconductor imager is disposed adjacent and contiguous to said first surface of said electronic interface substrate;
   c. a plurality of first electrical pads disposed on said first surface of said electronic interface substrate wherein some of said first electrical pads are disposed in a first row adjacent and contiguous to said first cut corner and the remainder of said first electrical pads are disposed in a second row adjacent and contiguous to said second cut corner whereby said first and second rows of said first electrical pads are aligned parallel to said first and second corners, respectively, of said electronic substrate;
   d. a plurality of second electrical pads disposed on said first surface of said semiconductor imager wherein some of said of second electrical pads are disposed in a first row adjacent and contiguous to said first cut corner and the remainder of said second electrical pads are disposed in a second row adjacent and contiguous to said second cut corner whereby said first and second rows of said second electrical pads are aligned parallel to said first and second corners, respectively, of said semiconductor imager; and
   e. a plurality of bond wires wherein each of said bond wires electrically couples one of said first electrical pads to one of said second electrical pads.

2. An intraoral x-ray imaging sensor according to claim 1 wherein said electronic interface substrate has a third cut corner and a fourth cut corner at its said mesial end and wherein said semiconductor imager has a third cut corner and a fourth cut corner at its said mesial end.

3. An intraoral x-ray imaging sensor according to claim 1 wherein said intraoral x-ray imaging sensor also includes an x-ray converter layer having a first surface and second surface and being substantially rectangular with a mesial end and a distal end wherein said x-ray converter layer has a first cut corner and a second cut corner at its said distal end and wherein said first surface of said x-ray converter layer is disposed adjacent to said first surface of said semiconductor imager whereby said x-ray converter layer converts x-rays into photons to be received by said semiconductor imager and said semiconductor imager samples and detects said converted x-rays as electrical signals.

4. An intraoral x-ray imaging sensor according to claim 3 wherein said x-ray converter layer has a third cut corner and a fourth cut corner at its said mesial end.

5. An intraoral x-ray imaging sensor according to claim 1 wherein said intraoral x-ray imaging sensor includes a housing and wherein said electronic interface substrate and semiconductor imager are disposed within said housing.

6. An intraoral x-ray imaging sensor according to claim 1 wherein said semiconductor imager is a CCD.

7. An intraoral x-ray imaging sensor according to claim 1 wherein said semiconductor imager is a CMOS detector.

8. An intraoral x-ray imaging sensor according to claim 5 wherein said housing has a top portion and bottom portion and wherein said intraoral x-ray imaging sensor includes a data cable which is mechanically coupled to said top portion of said housing and electrically coupled to said electronic interface substrate.

9. An intraoral x-ray imaging sensor according to claim 5 wherein said intraoral x-ray imaging sensor includes a wireless transmitter which is mechanically and electrically coupled to said electronic interface substrate.

10. An intraoral x-ray imaging sensor according to claim 5 wherein said housing is formed by encapsulation with an epoxy resin.

11. An intraoral x-ray imaging sensor comprising:
    a. an electronic interface substrate wherein said electronic interface substrate has a first surface and a second surface and is substantially rectangular with a mesial end and a distal end wherein said electronic interface substrate has a first cut corner and a second cut corner at its said mesial end;
    b. a semiconductor imager mechanically and electrically coupled to said electronic interface substrate wherein said semiconductor imager has a first surface and a second surface and consists of a silicon layer having an array of detector elements formed on its said first surface and is substantially rectangular with a mesial end and a distal end wherein said semiconductor imager has a first cut corner and a second cut corner at its said mesial end and wherein said second surface of said semiconductor imager is disposed adjacent and contiguous to said first surface of said electronic interface substrate;
    c. a plurality of first electrical pads disposed on said first surface of said electronic interface substrate wherein some of said first electrical pads are disposed in a first row adjacent and contiguous to said first cut corner and the remainder of said first electrical pads are disposed in a second row adjacent and contiguous to said second cut corner whereby said first and second rows of said first electrical pads are aligned parallel to said first and second corners, respectively, of said electronic substrate;
    d. a plurality of second electrical pads disposed on said first surface of said semiconductor imager wherein some of said of second electrical pads are disposed in a first row adjacent and contiguous to said first cut corner and the remainder of said second electrical pads are disposed in a second row adjacent and contiguous to said second cut corner whereby said first and second rows of said second electrical pads are aligned parallel to said first and second corners, respectively, of said electronic substrate; and e. a plurality of bond wires wherein each of said bond wires electrically couples one of said first electrical pads to one of said second electrical pads.

12. An intraoral x-ray imaging sensor according to claim 11 wherein said electronic interface substrate has a third cut corner and a fourth cut corner at its said distal end and wherein said semiconductor imager has a third cut corner and a fourth cut corner at its said distal end.

13. An intraoral x-ray imaging sensor according to claim 11 wherein said intraoral x-ray imaging sensor also includes an x-ray converter layer having a first surface and second surface and being substantially rectangular with a mesial end and a distal end wherein said x-ray converter layer has a first cut corner and a second cut corner at its said mesial end and wherein said first surface of said x-ray converter layer is disposed adjacent to said first surface of said semiconductor imager whereby said x-ray converter layer converts x-rays into photons to be received by said semiconductor imager and said semiconductor imager samples and detects said converted x-rays as electrical signals.

14. An intraoral x-ray imaging sensor according to claim 13 wherein said x-ray converter layer has a third cut corner and a fourth cut corner at its said distal end.

15. An intraoral x-ray imaging sensor according to claim 1 wherein said electronic interface substrate is a printed circuit board.

16. An intraoral x-ray imaging sensor according to claim 2 wherein said x-ray converter layer includes a fiber optic plate and a scintillating plate.

17. An intraoral x-ray sensor according to claim 6 wherein said electronic interface substrate has circuitry including a processor, a read only memory, a random access memory and an input/output module and is disposed on said second surface whereby said circuitry and said semiconductor imager combine to convert x-rays received through said bottom portion of said housing into x-ray data and output said x-ray data along said data cable.

18. An intraoral x-ray sensor according to claim 6 wherein said electronic interface substrate and said semiconductor imager are geometrically similar and wherein said electronic interface substrate is slightly larger than said semiconductor imager and they are basically congruent and said x-ray converter layer and said semiconductor imager are geometrically similar wherein said x-ray converter layer is slightly larger than said semiconductor imager and arranged such that none of the edges of said semiconductor imager projects over a corresponding edge of said x-ray converter layer.

* * * * *